(12) United States Patent
Eason et al.

(10) Patent No.: US 8,443,798 B2
(45) Date of Patent: *May 21, 2013

(54) INHALER

(75) Inventors: Stephen William Eason, Diss (GB);
Roger William Clarke, Histon (GB);
Quentin Harmer, Waterbeach (GB);
Peter Alan Evans, Ely (GB); David Gregory Ahern, Welney (GB)

(73) Assignee: Vectura Delivery Devices Limited, Chippenham, Wiltshire (GB)

( * ) Notice: Subject to any disclaimer, the term of this patent is extended or adjusted under 35 U.S.C. 154(b) by 139 days.

This patent is subject to a terminal disclaimer.

(21) Appl. No.: 12/985,976

(22) Filed: Jan. 6, 2011

(65) Prior Publication Data
US 2011/0132358 A1 Jun. 9, 2011

Related U.S. Application Data

(63) Continuation of application No. 10/575,615, filed as application No. PCT/GB2004/004416 on Oct. 18, 2004, now Pat. No. 7,950,389.

(30) Foreign Application Priority Data
Oct. 17, 2003 (GB) .................................. 0324358.1

(51) Int. Cl.
*A61M 11/00* (2006.01)

(52) U.S. Cl.
USPC ............. 128/203.12; 128/203.21; 128/203.15

(58) Field of Classification Search
USPC ............. 128/203.15, 203.12, 203.21, 200.14, 128/203.19, 203.23
See application file for complete search history.

(56) References Cited

U.S. PATENT DOCUMENTS

| | | | |
|---|---|---|---|
| 4,811,731 A | 3/1989 | Newell et al. | 128/203.15 |
| 4,824,517 A | 4/1989 | Leahy | |
| 5,533,502 A | 7/1996 | Piper | |
| 5,921,237 A | 7/1999 | Eisele et al. | |
| 6,032,666 A | 3/2000 | Davies et al. | 128/203.15 |
| 6,116,238 A | 9/2000 | Jackson et al. | 128/203.15 |
| 6,698,425 B1 | 3/2004 | Wilderstrom | |
| 6,880,555 B1 | 4/2005 | Brunnberg et al. | |

(Continued)

FOREIGN PATENT DOCUMENTS

| | | |
|---|---|---|
| EP | 0469814 | 2/1992 |
| EP | 0469814 | 2/1995 |

(Continued)

OTHER PUBLICATIONS

European Search Report dated Sep. 2, 2011.

*Primary Examiner* — Steven Douglas
(74) *Attorney, Agent, or Firm* — Davidson, Davidson & Kappel, LLC

(57) ABSTRACT

An inhaler is disclosed. It comprises a housing to receive a strip of blisters each having a puncturable lid and containing a dose of medicament for inhalation by a user, a mouthpiece through which a dose of medicament is inhaled by a user and, an actuator operable to sequentially move each blister into alignment with a blister piercing member. The actuator is also operable to cause the blister piercing element to puncture the lid of a blister such that, when a user inhales through the mouthpiece, an airflow through the blister is generated to entrain the dose contained therein and carry it out of the blister and via the mouthpiece into the user's airway.

19 Claims, 21 Drawing Sheets

U.S. PATENT DOCUMENTS

| | | |
|---|---|---|
| 6,907,880 B1 | 6/2005 | Heckenmuller et al. |
| 6,948,496 B2 | 9/2005 | Eason et al. ............. 128/203.15 |
| 7,520,278 B2 | 4/2009 | Crowder et al. |
| 7,950,389 B2 * | 5/2011 | Eason et al. ............. 128/203.12 |
| 2002/0032409 A1 | 3/2002 | Ritsche ................... 128/200.14 |
| 2004/0211419 A1 | 10/2004 | Eason et al. ............. 128/203.15 |
| 2006/0292082 A1 | 12/2006 | Sarkar et al. ............. 128/203.12 |
| 2007/0074721 A1 | 4/2007 | Harmer et al. ........... 128/203.15 |

FOREIGN PATENT DOCUMENTS

| | | |
|---|---|---|
| FR | 2516387 | 5/1983 |
| FR | 2701653 | 8/1994 |
| GB | 2 122 903 | 1/1984 |
| GB | 2340758 | 8/1998 |
| GB | 2 340 758 | 3/2000 |
| JP | 5123399 | 7/1991 |
| JP | 4507357 | 12/1992 |
| JP | 5504081 | 7/1996 |
| JP | 2002506686 | 3/2002 |
| WO | 9013328 | 11/1990 |
| WO | 9102558 | 3/1994 |
| WO | 9947099 | 9/1999 |
| WO | 0126720 | 4/2001 |
| WO | WO 01/26720 | 4/2001 |
| WO | 03077979 | 9/2003 |

* cited by examiner

INHALER

This application is a continuation of U.S. patent application Ser. No. 10/575,615 which is a national phase application under 35 U.S.C. §371 of International Application No. PCT/GB2004/004416, filed Oct. 18, 2004 which claims priority to Great Britain Application No. 0324358.1 filed Oct. 17, 2003, the disclosures of which are all hereby incorporated by reference herein.

FIELD OF THE INVENTION

The present invention relates to an inhalation device for oral or nasal delivery of medicament in powdered form. The invention also relates to an inhaler containing a strip of blisters each having a puncturable lid and containing a dose of medicament for inhalation by a user of the device according to the invention and, to a method of using such a device.

BACKGROUND OF THE INVENTION

Oral or nasal delivery of a medicament using an inhalation device is a particularly attractive method of drug administration as these devices are relatively easy for a patient to use discreetly and in public. As well as delivering medicament to treat local diseases of the airway and other respiratory problems, they have more recently also been used to deliver drugs to the bloodstream via the lungs thereby avoiding the need for hypodermic injections.

In one type of conventional metered dose inhalation device, the powdered medicament is held in a reservoir within a dispensing device that is operable to measure out and dispense a predetermined amount of powder for each dose. However, these devices suffer from poor dose metering capability especially when the size of the dose is relatively small as it is difficult to accurately measure out small amounts of dry powder in such a device. It is also difficult to protect the drug from the ingress of moisture and to seal it from the atmosphere until it is required for administration to a patient.

It is common for dry powder formulations to be pre-packaged in individual doses, usually in the form of capsules or blisters which each contain a single dose of the powder which has been accurately and consistently measured. A blister is generally cold formed from a ductile foil laminate or a plastics material and includes a puncturable lid which is permanently heat-sealed around the periphery of the blister during manufacture and after introduction of the dose into the blister. A foil blister is preferred over capsules as each dose is protected from the ingress of water and penetration of gases such as oxygen in addition to being shielded from light and UV radiation all of which can have a detrimental effect on the delivery characteristics of the inhaler if a dose becomes exposed to them. Therefore, a blister offers excellent environmental protection to each individual drug dose.

Inhalation devices that receive a blister pack comprising a number of blisters each of which contain a pre-metered and individually packaged dose of the drug to be delivered are known. Actuation of the device causes a mechanism to open a blister so that when the patient inhales, air is drawn through the blister entraining the dose therein that is then carried out of the blister through the device and via the patient's airway down into the lungs.

It is advantageous for the inhaler to be capable of holding a number of doses to enable it to be used repeatedly over a period of time without the requirement to open and/or insert a blister into the device each time it is used. Therefore, many conventional devices include means for storing a number of blisters each containing an individual dose of medicament. When a dose is to be inhaled, an indexing mechanism moves a previously emptied blister away from the opening mechanism so that a fresh one is moved into a position ready to be opened for inhalation of its contents.

A problem with conventional inhalation devices is that they are relatively large, heavy and difficult to operate. Despite their large size, many of them only have sufficient capacity to hold a relatively small number of doses before the device must be opened and a fresh set of blisters mounted therein. Although it may be possible to increase the number of blisters by making them smaller, this can only be achieved at the expense of reducing the dose payload or capacity of each blister. This is particularly disadvantageous when the device is to be used to deliver for example newer, less potent drugs where each blister must be able to hold a payload of somewhere in the region of 10-20 mg of the drug.

Due to their nature and method of operation, conventional inhalation devices have a relatively complicated construction and consist of many separate components making them difficult and time consuming to assemble as well as being expensive to manufacture and purchase.

A conventional inhalation device of the type described above is known from U.S. Pat. No. 4,811,731. This device is configured to receive a disc-shaped dose storage blister pack in which the doses are arranged in a generally circular pattern. A plunger is provided which moves in response to the actuation of a lever to puncture a blister disposed beneath it to enable the dose to be inhaled from the punctured blister. The device also includes a separate indexing device operable to rotate the disc so as to move a fresh blister to a puncturable position. A significant problem with this device is that the number of doses is severely limited. As can be seen from the device shown in the Figures, it is capable of receiving only eight doses at a time so frequent replacement of the disc is necessary. Although it will be appreciated that the disc can be made larger to accommodate a larger number of blisters, this would result in a significant increase in the overall size of the device making it very bulky. It is also notable that the piercing and indexing steps are controlled entirely independently of each other making the device significantly harder to use and increasing the number of components forming the device.

Another known inhalation device is described in U.S. Pat. No. 6,032,666. Although this device receives a strip of blisters, it has a very complicated construction with numerous components making it hard to assemble and operate. It is limited by the fact that access to the dose contained in each blister is obtained by peeling the lid off it rather than by piercing it. Therefore, the device has a complicated mechanism for peeling the lid from the blister including a take-up spool for the peeled lid strip and a complex clutch arrangement to ensure that the same length of lid is peeled from the strip each time the device is used as more and more of the lid strip is wound around the take-up spool. These components, together with the requirement to store the peeled lid within the device, increases its complexity and overall size as well as making it harder to re-fill with a fresh strip of blisters. It will also be appreciated that this device can only be used with a strip of blisters in which the lid is peelably attached to the blister. Not only does this require a suitable adhesive, it also reduces the barrier to moisture and other environmental contaminants.

SUMMARY OF THE INVENTION

The present invention seeks to provide an inhalation device that overcomes or substantially alleviates the problems with conventional inhalation devices of the type discussed above. In particular, the invention seeks to provide a device having a significantly simpler construction than known devices that is capable of storing a relatively large number of blisters that are also capable of containing a large payload without any significant increase in the overall size of the device. The inhalation device of the present invention should also be much easier to make, assemble and operate as well as being cheaper to manufacture.

According to the invention, there is provided an inhaler comprising a housing to receive a plurality of blisters each having a puncturable lid and containing a dose of medicament for inhalation by a user, a mouthpiece through which a dose of medicament is inhaled by a user and, an actuator operable to sequentially move each blister into alignment with a blister piercing member, said actuator also being operable to cause the blister piercing member to puncture the lid of a blister such that, when a user inhales through the mouthpiece, an airflow through the blister is generated to entrain the dose contained therein and carry it out of the blister and via the mouthpiece into the user's airway.

In a preferred embodiment, the actuator is pivotally mounted to the housing and may comprise an arm which may be pivotally mounted to the housing at one end. The blister piercing member may comprise a pair of piercing heads depending from one side of said arm positioned so as to extend through the aperture in the housing in a closed position, in which the arm lies substantially against the housing, to pierce the lid of a blister aligned with the aperture.

Each piercing head may preferably comprise a primary cutting element and a pair of secondary cutting elements extending laterally across each end of the primary cutting element. Conveniently, the primary cutting element and the secondary cutting elements each have a pointed tip, the tip of the primary cutting element extending beyond the tips of each of the secondary cutting elements. Ideally, the secondary cutting elements are parallel to each other and extend at right angles to the primary cutting element, although the secondary elements need not be parallel and could extend from the primary cutting element at any convenient angle.

In a preferred embodiment, an opening is formed in the arm in the vicinity of each piercing head, at least one of said openings forming an airflow inlet to a blister and, at least one other of said openings forming an airflow outlet from a blister. Conveniently, the secondary cutting elements upstand from the edge or periphery of said opening in the arm and the primary cutting element extends across the opening and joins each of the secondary cutting elements together.

Advantageously, the mouthpiece is on the arm and extends in a direction opposite to the direction in which the piercing heads extend, the openings in the arm being in communication with the inside of the mouthpiece. In one embodiment, the mouthpiece, the arm and the piercing heads are integrally formed, although the piercing heads may also be formed on a separate piercing module that is removably mountable on the arm or is at least separately attachable to the arm during manufacture.

The mouthpiece preferably includes a primary chamber having an outside air inlet in communication, via the primary chamber, with the or each airflow inlet opening in the arm and, a secondary chamber in communication with the or each airflow outlet opening in said arm such that, when a user inhales through the mouthpiece, air is drawn through the or each airflow inlet opening into the blister via the outside air inlet and the primary chamber to entrain the dose in the airflow, said entrained dose passing through the or each airflow outlet openings into the secondary chamber of the mouthpiece from where it is carried into the user's airway.

A partitioning wall may separate the primary and secondary chambers within the mouthpiece and at least one air bypass aperture may extend through the partitioning wall to communicate the primary chamber with the secondary chamber. As air can pass directly from the primary to the secondary chambers when a user inhales, in addition to passing through the blister, the effort required to inhale through the mouthpiece is reduced.

The or each bypass aperture may be configured such that the airflow from the primary chamber into the secondary chamber through the or each bypass aperture and the airflow from the or each airflow outlet openings meet substantially at right angles to each other. As the flows meet at an angle, the degree of turbulence is increased which assists in the deagglomeration of the dose and the creation of an inhalable aerosol.

In a preferred embodiment the inhaler includes an indexing mechanism including an indexing member that moves so as to move a blister into alignment with the blister piercing member. Most preferably, the indexing member is a wheel which rotates so as to move a blister into alignment with the blister piercing member. However, it is also envisaged that other arrangements are possible such as, for example, a mechanism that incorporates a sliding or reciprocating member.

In a preferred embodiment, the inhaler is configured so that indexing of the blister strip occurs when the actuator is pivoted in one direction and piercing of a blister occurs when it is rotated in the opposite direction. However, the device can also be configured so that the indexing wheel rotates, to move a blister into alignment with said blister piercing member, in response to rotation of the actuator with respect to the housing in one direction, movement of the actuator in the same direction also being operable to puncture the lid of a blister aligned with the blister piercing member.

Preferably the indexing wheel and the actuator include co-operating means thereon that engages when the actuator is rotated in one direction to cause rotation of the indexing wheel.

In one embodiment, the cooperating means comprise a set of ratchet teeth on the indexing wheel and a drive pawl on the actuator.

Advantageously, means depend from the housing to substantially prevent rotation of the indexing wheel other than by movement of the actuator in said one direction.

In one embodiment said means comprises a first resiliently deformable anti-rotation pawl on the housing that extends into one of said recesses in the indexing wheel, the actuator including means for deflecting the first anti-rotation pawl from the recess to permit rotation of the indexing wheel when the drive pawl engages with the ratchet teeth.

The actuator may include a drive plate and the means on the actuator for deflecting the first anti-rotation pawl comprises a release pin upstanding from the drive plate that engages with and resiliently deflects the pawl out of the recess to allow rotation of the indexing wheel.

The inhaler may also comprise a second resiliently deformable anti-rotation pawl on the housing and a cam member on the actuator, the cam member engaging with a cam surface on the second anti-rotation pawl when the first anti-rotation pawl is deflected out of a recess to prevent rotation of the indexing wheel through more than a predetermined angle.

The inhaler may include a cap attached to the housing pivotable between a closed position in which it covers the actuator and mouthpiece and an open position in which the actuator and mouthpiece are revealed to enable a user to inhale through the mouthpiece.

In another embodiment of the invention, the indexing wheel rotates to move a blister into alignment with the blister piercing member in response to rotation of the cap with respect to the housing from the open to the closed position. This embodiment simplifies the operation of the device even further by providing that the piercing and indexing steps are performed in response to opening and closing of the cap that locates over the mouthpiece.

Preferably, the cap and the actuator include co-operating means to couple the actuator to the cap such that the actuator rotates relative to the housing in response to rotation of the cap between the open and closed positions.

The cooperating means may comprise a cam guide slot on the cap and a cam follower on the actuator slideably located within the cam guide slot. Ideally, the cam guide slot is shaped such that when the cap is rotated from its closed to its open position, the cam follower travels along the cam guide slot to rotate the actuator and cause the blister piercing member to pierce a blister aligned therewith the aperture and, when the cap is rotated from its open to its closed position, the cam travels back along the cam guide slot to cause the actuator to rotate in the opposite direction and withdraw the piercing member from the blister. Furthermore, the cam guide slot may be configured so that the actuator does not rotate until towards the end of the movement of the cap from its closed to its open position and rotates at the beginning of the movement of the cap from its open to its closed position.

In a preferred arrangement, the indexing wheel and the cap each include a toothed gear member mounted thereon engaged such that rotation of the cap between the open and closed positions causes rotation of the gear member on the indexing wheel.

A clutch member preferably couples the gear member on the indexing wheel to the indexing wheel such that the indexing wheel rotates together with the gear member coupled thereto when the cap is rotated from the open to the closed position to move a subsequent blister into alignment with the blister piercing member.

The housing advantageously includes a chamber to receive used blisters. The chamber may be covered by a lid attached to the housing which is openable to facilitate removal of a portion of used blisters from the blisters remaining in the device.

In one embodiment, a separating element is mounted on the housing, which is operable to enable detachment of said portion of used blisters. The separating element preferably includes a resilient blister grip that is operable to press a blister strip against the housing to facilitate separation of said portion from said remaining blisters.

The inhaler according to the invention may also incorporate a coiled strip of blisters, each having a puncturable lid and containing a dose of medicament for inhalation by a user, located in the housing.

According to the invention, there is also provided a method of using an inhaler according to the invention including the step of rotating the actuator to move a blister into alignment with a blister piercing member in the housing and to puncture the lid of a blister aligned with the blister piercing member and, inhaling through the mouthpiece to generate an airflow through the blister to entrain the dose contained therein and carry it through the aperture and via the mouthpiece into the user's airway.

The step of rotating the actuator may include the step of rotating it in a first direction to puncture the lid of a blister aligned with the blister piercing member and, once the inhalation step is complete, rotating it in a second direction to move a subsequent blister into alignment with the blister piercing member in the housing. Additionally, the step of rotating the actuator may comprise the step of rotating a cap coupled to the actuator.

According to another aspect of the invention, there is provided an inhaler comprising a housing to receive a blister having a puncturable lid and containing a dose of medicament for inhalation by a user, the device comprising a piercing head for puncturing the lid of a blister so that the dose contained therein can be inhaled by the user from the blister through the device, wherein the piercing head comprises a primary cutting element which is configured to cut, as the piercing head enters the blister, a first linear slit in the lid and, secondary cutting elements extending laterally from the primary cutting element which are configured to cut, as the piercing head continues to enter the blister, second linear slits that extend across each end of the first linear slit formed by the primary cutting element, the primary and secondary cutting elements together forming a pair of flaps in the lid which are folded aside by the piercing head upon further entry of the piercing head into the blister.

The inhaler may be capable of receiving just a single blister. However, in a preferred embodiment, it receives a strip of blisters each containing a dose of medicament. In this case, the inhaler may include a blister strip indexing mechanism, such as those described with reference to other embodiments of the invention, which is operable to cause the blister strip to sequentially index the blisters into a position in which each blister will be pierced by the piercing head.

In a preferred embodiment, the piercing head comprises a pair of secondary cutting elements. The secondary cutting elements may be spaced from each other and the primary cutting element is mounted on and extends between said pair of secondary cutting elements.

Preferably, the primary cutting element is formed from a blade, the plane of the blade lying substantially at right angles to a plane occupied by the lid of a blister, which is located in the inhaler in a position ready for piercing.

The primary cutting element advantageously has a sharpened edge for cutting the first linear slit in the lid of the blister. The edge may taper towards a pointed tip which may be located midway between the secondary cutting elements.

The secondary piercing elements are positioned so that they each extend laterally across either end of the primary piercing element.

Each of the secondary piercing elements may be formed from a blade, the plane of the blade lying substantially at right angles to the plane of the blade forming the primary piercing element and at tight angles to the lid of a blister located in a piercing position. As with the primary piercing element, each of the secondary piercing elements may have a sharpened edge to cut the second linear slits in the lid of a blister.

The edge of each of the secondary piercing elements taper to a pointed tip.

In a preferred embodiment, the pointed tip of each of the secondary piercing elements lie in the plane occupied by the primary piercing element.

Conveniently, the pointed tip of each of the secondary piercing elements lie at the same height as the primary piercing element at the point at which the primary piercing element and secondary piercing element meet each other.

In another embodiment, the primary cutting element divides each secondary cutting element into first and second cutting members that extend laterally from opposite sides of the primary cutting element.

Preferably, the first and second cutting members converge towards each other at an angle and the primary cutting element upstands from the top of the secondary cutting members from a point on each secondary cutting element at which the first and second cutting members meet.

The secondary cutting elements may be angled inwardly towards each other to assist in the formation and folding of the flaps in the lid of the blister as the piercing head enters the blister.

The inhaler preferably comprises a pair of piercing heads upstanding from a piercing member.

Preferably, the primary and secondary cutting elements are integrally moulded in one piece.

In a preferred embodiment, the secondary cutting elements extend laterally from the primary cutting element at an angle of 90 degrees to the primary cutting element. However, it is also envisaged that the secondary cutting elements may extend laterally from the primary cutting element at an angle of less than, or more than, 90 degrees.

The primary cutting element preferably divides each of the secondary cutting elements into secondary cutting members that extend laterally from the primary cutting element by different distances so that the flap cut in the lid of a blister by the secondary cutting members extending laterally from one side of the primary cutting element is of a different size to the flap cut in the blister by the secondary cutting members that extend laterally from the other side of the primary cutting member.

According to any of the embodiments of the invention, the piercing member may comprise a discrete piercing module which is moulded separately and then subsequently attached to the actuator either permanently during assembly or so that it may be removed from the actuator by the user for replacement, if necessary. The piercing module conveniently comprises a main body portion with first and second piercing heads upstanding therefrom.

Preferably, an air inlet and an air outlet aperture extends through the main body portion of the piercing module, one of the piercing heads depending from the periphery of the air inlet and extending over the air inlet and the other piercing head depending from the periphery of the air outlet and extending over the air outlet.

The main body portion may include a recessed region around the air inlet, the piercing head depending from the periphery of the air inlet from the recessed region.

The air outlet aperture is preferably in communication with an air outlet tube extending from the main body in an opposite direction to the piercing head extending from the periphery of the air outlet aperture.

In a preferred embodiment, the air outlet tube comprises axially extending ridges formed on its outer surface, which locate the piercing head within a walled recess in the mouthpiece.

A space formed between the ridges and the walled recess advantageously comprises a bypass air conduit for the direct flow of air into the mouthpiece from outside when a patient inhales through the mouthpiece.

In a preferred embodiment, the indexing mechanism comprises a blister strip locator chassis defining a path for the strip of blisters past the aperture in the housing.

Preferably, a resiliently deformable arm extends from the blister strip locator chassis and the indexing mechanism comprises an indexing wheel rotatably mounted to the free end of the resiliently deformable arm over which a strip of blisters is passed.

The indexing wheel may comprise a set of spokes and the actuator includes a drive tooth engageable with a first spoke when the actuator is pivoted relative to the housing into an open position to cause the indexing wheel to rotate together with the actuator to index the blister strip.

Preferably the inhaler includes an anti-rotation ramp on the housing which is engaged by another spoke of the indexing wheel when the indexing wheel rotates thereby causing the arm to deform to allow said spoke to clear the anti-rotation ramp, the arm returning to its undeformed state once the spoke has cleared the ramp, thereby preventing rotation of the indexing wheel in the opposite direction.

Preferably, the drive tooth on the actuator is shaped so that, when the actuator is rotated in the opposite direction from its open into its closed position, the drive tooth slides over the top of the preceding spoke of the indexing wheel.

Conveniently, the edge of each spoke is shaped to allow the drive tooth to pass over it when the actuator is pivoted from its open into its closed position.

In one embodiment, a location ramp may be positioned adjacent to but spaced from the anti-rotation ramp. In this case, the drive tooth may be operable to cause the arm to resiliently deform as the drive tooth slides over the top of the spoke to cause another spoke of the indexing wheel to extend into the space between the anti-rotation and location ramps and prevent rotation of the indexing wheel in either direction.

Embodiments of the invention will now be described, by way of example only, with reference to the accompanying drawings, in which:—

DETAILED DESCRIPTION OF THE INVENTION

A first embodiment of the inhaler according to the invention will be described with reference to FIGS. 1 to 10. This embodiment provides a simple, easy to use inhalation device that indexes and pierces a blister using the same actuator. Furthermore, the actuator both indexes and pierces a blister during the same stroke or direction of rotation of the actuator.

Figure 1:
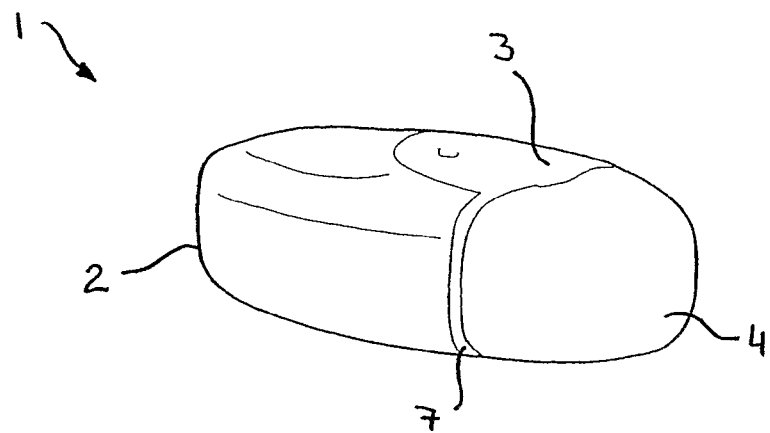
FIG. 1 is a perspective view of an inhaler according to an embodiment of the invention.
Figure 2:
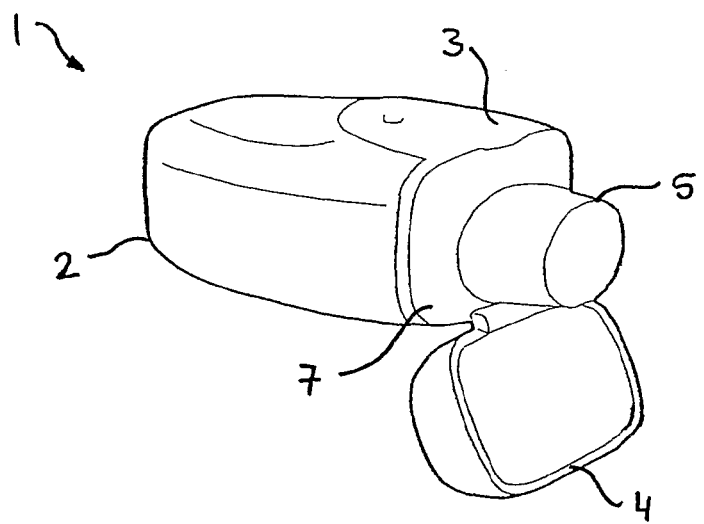
FIG. 2 is a perspective view of the inhaler illustrated in FIG. 1 with the cap open to reveal the mouthpiece and the actuator in a closed position.

Referring now to the drawings, there is shown in FIG. 1 an inhaler 1 according to a first embodiment of the invention comprising a housing 2 to which is pivotally mounted an actuator 3. A cap 4 is integrally hinged to the top edge of the housing 2 and is pivotable between a closed position, as shown in FIG. 1, to an open position, as shown in FIG. 2, to gain access to a mouthpiece 5 integrally formed with and upstanding from the actuator 3. The cap 4 completely covers and protects the mouthpiece 5 when closed and prevents contamination thereof or the possible ingress of dirt into the housing 2 which could otherwise be inhaled when the device is used.

The inhaler 1 is intended for use with a strip 6 of moisture proof blisters (see FIG. 13) each containing a pre-measured dose of powdered medicament for inhalation. Each blister 6a in the strip 6 comprises a generally hemispherically shaped pocket 6b and a flat puncturable lid 6c permanently heat sealed to the pocket 6b to hermetically seal the dose therein. The strip 6 is preferably manufactured from foil laminate or a combination of foil laminate, such as aluminium, and plastics material.

In a preferred embodiment the blisters consist of a base and a lid. The base material is a laminate comprising a polymer layer in contact with the drug, a soft tempered aluminium layer and an external polymer layer. The aluminium provides the moisture and oxygen barrier, whilst the polymer provides a relatively inert layer in contact with the drug. Soft tempered aluminium is ductile so that it can be "cold formed" into a blister shape. It is typically 45 μm thick. The outer polymer layer provides additional toughness to the laminate. The lid material is a piercable laminate comprising a heat seal lacquer, a hard rolled aluminium layer (typically 20-30 μm thick) and an external lacquer layer. The heat seal lacquer bonds to the polymer layer of the base foil laminate during heat sealing. Materials for the polymer layer in contact with the drug include poly vinyl chloride (PVC), polypropylene (PP) and polyethylene (PE). In the case of PE, the heat seal lacquer on the foil lid is replaced with a further layer of PE. On heat-sealing, the two layers of PE melt and weld to each other. The external polymer layer on the base foil is typically oriented polyamide (oPA).

Figure 3:
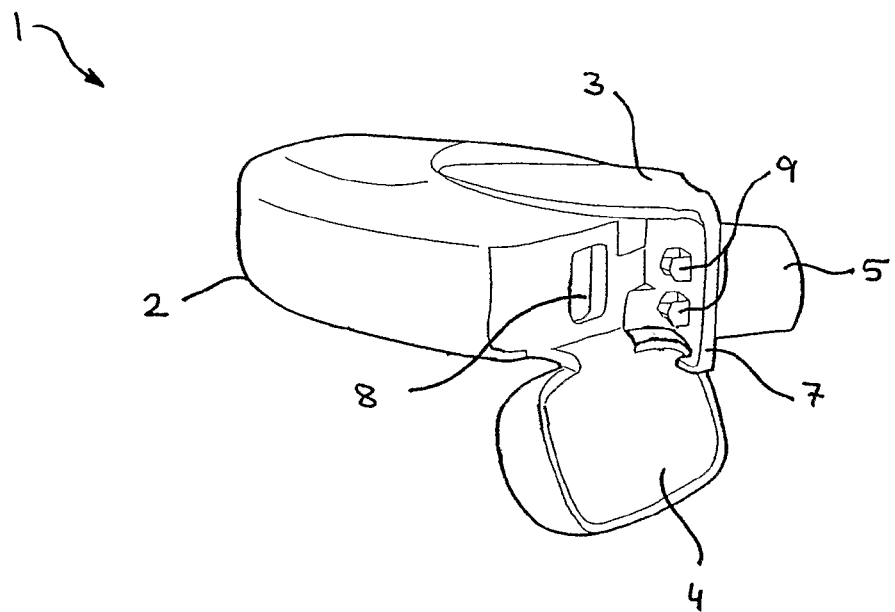
FIG. 3 is a perspective view of the inhaler illustrated in FIG. 2 with the actuator in an open position.
Figure 4:
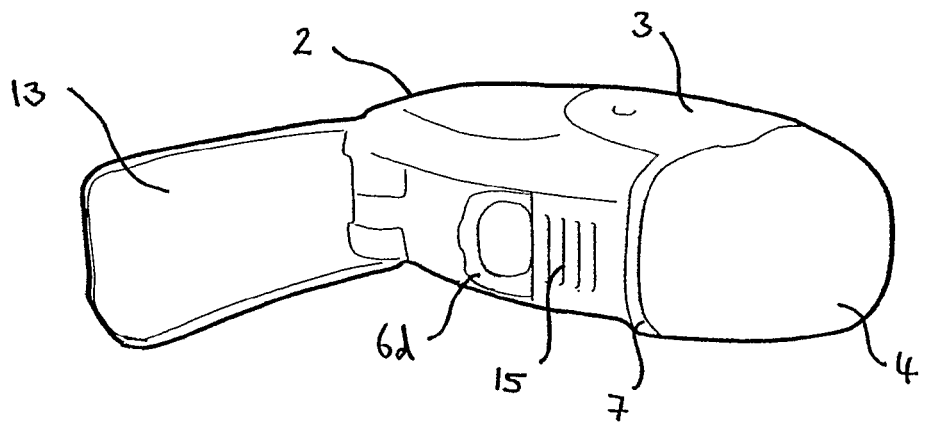
FIG. 4 is a perspective view of the inhaler shown in FIG. 1 with a used blister chamber cover open.

The actuator 3 comprises a lever arm 7 having one end pivotally mounted to the housing 2 to enable it to rotate from a closed position shown in FIGS. 1, 2 and 4 into an open position shown in FIG. 3. As can be seen from FIG. 3, the housing 2 has an aperture 8 therein to receive a piercing member comprising a pair of piercing heads 9 that extend from the lever arm 7 when the actuator 3 is in a closed position and penetrate the lid 6c of a blister located within the housing 2 immediately behind the aperture 8.

The shape of the piercing heads 9 will now be described with reference to FIG. 8A. This is important because the openings that are made in the lid 6c of a blister 6a must be of a sufficient cross-sectional area and shape to promote the free-flow of air through the blister 6a and to ensure that all of the internal volume of the blister 6a is swept by the airflow and consequently that all, or substantially all, of the dose is entrained and carried out of the blister 6a. Each piercing head 9 comprises a generally "H" shaped element having a flat blade-like central tooth or primary cutting element 10 and a pair of flat blade-like end teeth or secondary cutting elements 11 extending laterally across each end of the primary piercing element 10. Each of the primary and secondary cutting elements 10,11 taper to a pointed tip. The pointed tip 10a of the primary cutting element 10 may be located in its centre i.e. midway between the secondary cutting elements 11. However, it may be advantageous to form the primary cutting element 10 so that its pointed tip 10a is closer to one of the secondary piercing elements 11 than the other secondary cutting element 11, for example in order to facilitate correct piercing when the angle of approach of the piercing heads 9 is not normal to the foil. The height of each of the secondary cutting elements 11 is such that the pointed tips 11a of the secondary cutting elements 11 are at the same height as the edges of the primary cutting element 10 where the primary and secondary cutting elements 10,11 meet each other. The pointed tip 10a of the primary cutting element 10a is therefore above the pointed tip 11a of each of the secondary cutting elements 11 so that the primary cutting element 10 slits, or has at least initiated, the first linear slit in the blister before either of the secondary cutting elements 11 begin to cut the second linear slits in the blister. The top edges of each primary and secondary cutting elements 10,11 are sharpened to enable them to easily penetrate and cut the lid 6c of a blister 6a.

Figure 8A:
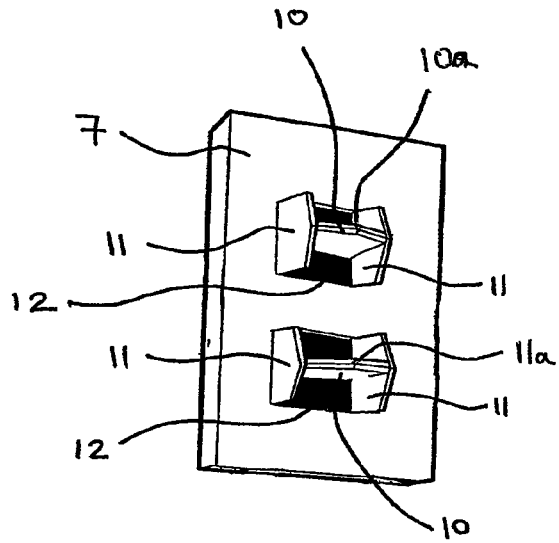
FIGS. 8A and 8B shows the configuration of the piercing elements on the actuator and a small portion of a strip of blisters to illustrate the type of cut made therein by the piercing elements, respectively.

As can be seen in FIG. 8A, the secondary cutting elements 11 of each piercing head 9 upstand from opposite edges of an aperture 12 in the lever arm 7 to enable the flow of air through the arm 7 into and out of the blister 6b via the holes made in the lid 6c of the blister 6b with the piercing members 9. The primary cutting element 10 is attached to, and is supported between, each of the secondary cutting elements 11 and the primary cutting element extends across the aperture 12 and so is not attached directly to the lever arm 7.

Figure 8B:
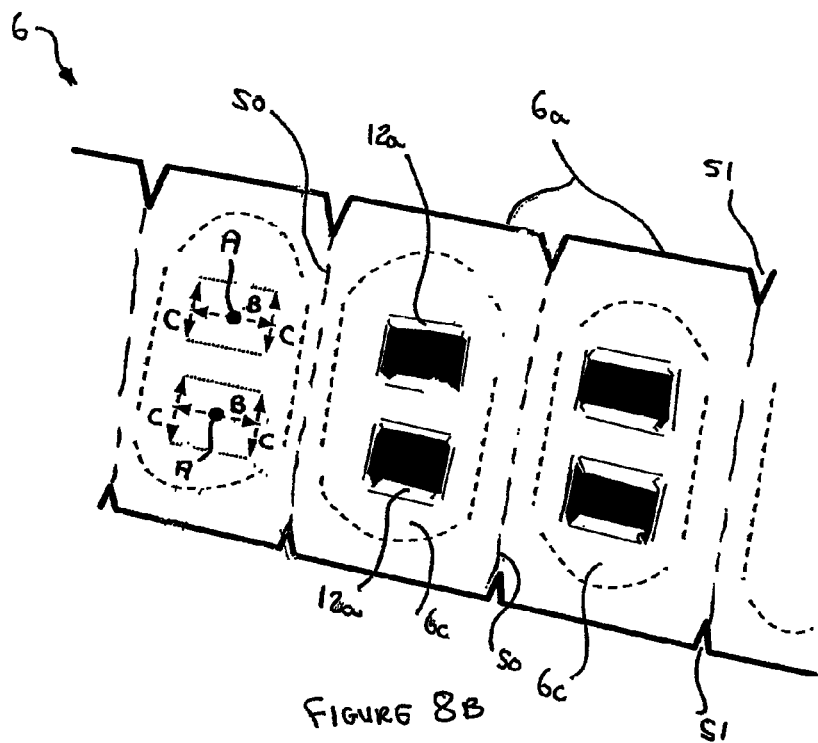

FIG. 8B illustrates a short section of a strip 6 of blisters 6a to show the shape and size of the openings that each of the piercing elements 9 described with reference to FIG. 8A cut in the lid 6c of a blister 6b. The primary cutting elements 10 penetrate the lid 6c first (point A in FIG. 8B) and, as they enter the blister 6a, two linear cuts or slits are made by each of them, as indicated by arrows "B". As the piercing head further enters the blister, the secondary cutting elements 11 penetrate the blister 6a and further linear cuts are made at each end of the linear cuts perpendicular to the first linear cut formed by the primary piercing element 10, as indicated by arrows "C". These cuts have the effect of creating flaps 12a that are folded back into the blister 6a as the piercing head 9 enters further into the blister. These piercing heads 9 are capable of forming openings that extend to over 30 to 50% of the surface area of a lid 6c of a blister 6a. For example, in the embodiment of FIG. 27, the blister lid area is 67 mm$^2$ and the piercers open an area of 29 mm$^2$ which is equivalent to 43% of the surface area of the lid.

As shown in FIG. 4, a cover 13 is pivotally attached to the side of the housing 2 and encloses a space to receive used blisters 6d that are fed into said space through a slot 14 in the wall of the housing 2. The space within the cover 13 is large enough to accommodate only a few used blisters 6d therein and so a resiliently flexible blister grip 15 extends from the housing 2 and facilitates removal of some of the used blisters 6d from the blisters 6 that remain in the housing 2. To remove a section of used blisters 6d, the blister grip 15 is pressed against the strip 6 to sandwich it between the blister grip 15 and the sidewall of the housing 2. The visible section of used blisters 6d can then be grasped in the hand, torn off and discarded without inadvertently placing undue force on the remaining part of the blister strip 6 that would tend to pull it out of the housing 2. FIGS. 10A to 10C show three front cross-sectional views through the inhaler 1. In FIG. 10A, there are no empty blisters 6d protruding through the slot 14. In FIG. 10B, the device has been activated twice more and so two empty blisters 6d have now passed through the slot 14. In FIG. 10C, the blister grip 15 has been pressed against the housing 2 in the direction of arrow "A" to enable the two empty blisters 6d to be detached by pulling them in the direction of arrow "B".

It will be appreciated that a cover 13 is not essential and the used blisters 6d may be removed as soon as they emerge from the aperture 14 in the wall of the housing 2. In another embodiment, the inhaler 1 may be provided with a cutting implement (not shown) such as a blade or serrations against which the section of used blisters 6d to be removed may be pressed to facilitate their detachment. In a preferred arrangement, a blade may be mounted to and extend from the blister grip 15 so that when it is pressed against the housing 2 it cuts the strip 6d located between the blister grip 15 and the housing 2. In yet another embodiment, the inhaler 1 may incorporate a larger chamber possibly with a take-up spool around which the used blister strip 6d may be wound so that it can be removed as a whole from the device and so avoid the need to detach sections of the strip 6d as each short section of blisters 6a are used up. However, in order to keep the device as small as possible, it is preferable to provide an arrangement in which at least some of the used blisters 6d can easily be removed from the device whilst unused blisters remain in it.

Figure 5:
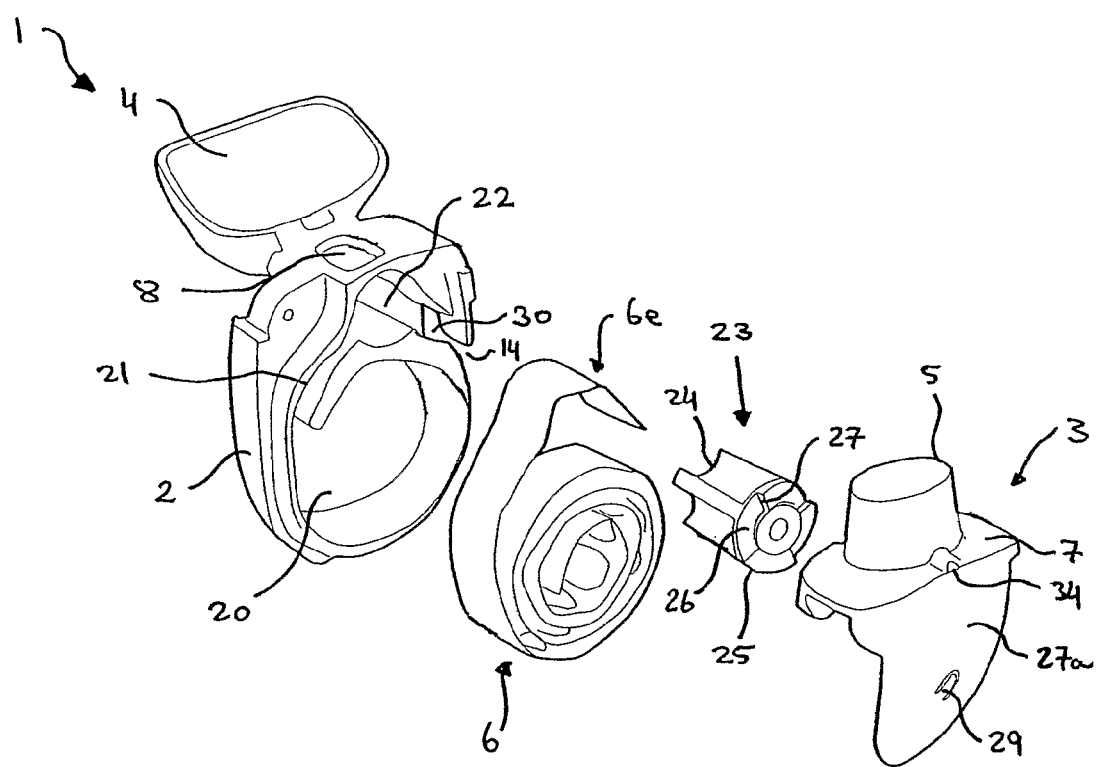
FIG. 5 is an exploded perspective view of the inhaler illustrated in FIGS. 1 to 4 also showing a coiled strip of blisters used with the device according to the invention.

Referring now to FIG. 5, the housing 2 comprises a generally cylindrically shaped chamber 20 to receive a coiled or wound strip of blisters 6 each containing a pre-measured dose of medicament to be delivered using the inhaler 1. The leading end 6e of the strip 6 is received in a blister feed inlet path 21 which opens up into a generally cylindrical cavity 22 adjacent to and in communication with the aperture 8 in the housing 2 and in which is rotatably received an indexing wheel 23. A used blister feed outlet path 30 extends from the cylindrical cavity 22 and leads to the aperture 14 in the wall of the housing 2.

The chamber 20 has a cover (not shown in FIG. 5) that forms part of the housing 2. Preferably, the cover is removably attached to the remainder of the housing 2 to enable access to the inside of the inhaler 1 to be obtained to enable a fresh strip 6 of blisters to be inserted therein. However, it is envisaged that the device could form a disposable unit in which case a strip of blisters 6 could be mounted in the device during assembly and the cover permanently attached so that once the strip has been exhausted, the whole device is thrown away. The simplicity of the construction of the device and the relatively few separate components make the device very cheap to manufacture and so a disposable unit is a viable proposition.

Figure 13:
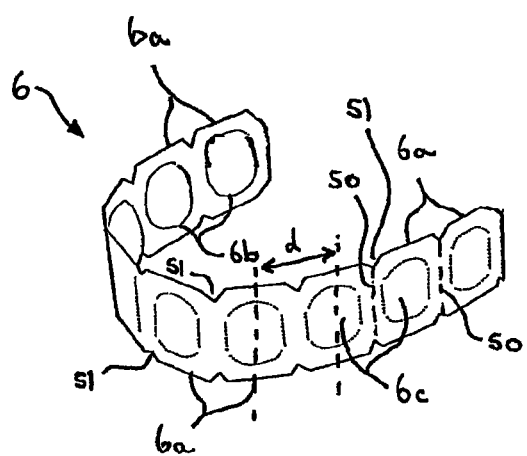
FIG. 13 shows a short portion of a strip of blisters for use in the inhaler according to any embodiment of the invention.
Figure 14:
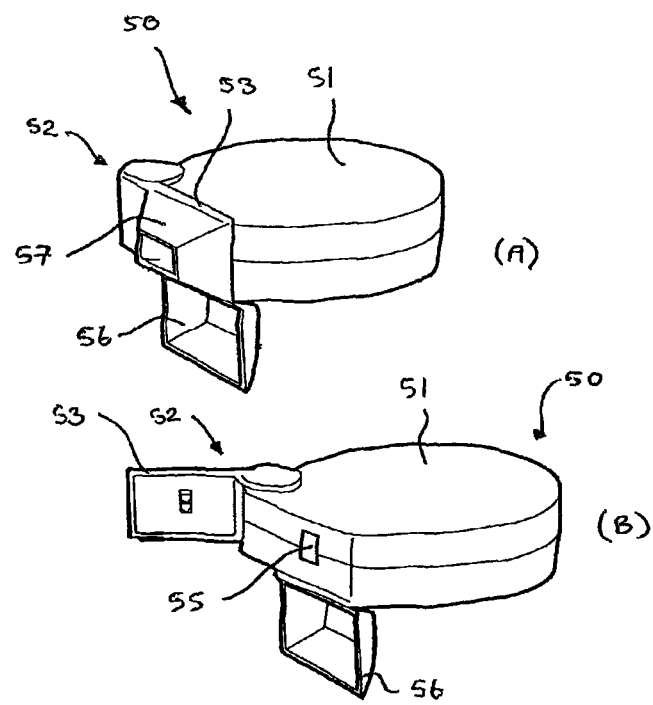
FIGS. 14A and 14B are perspective views of another embodiment of inhaler according to the present invention.
Figure 15:
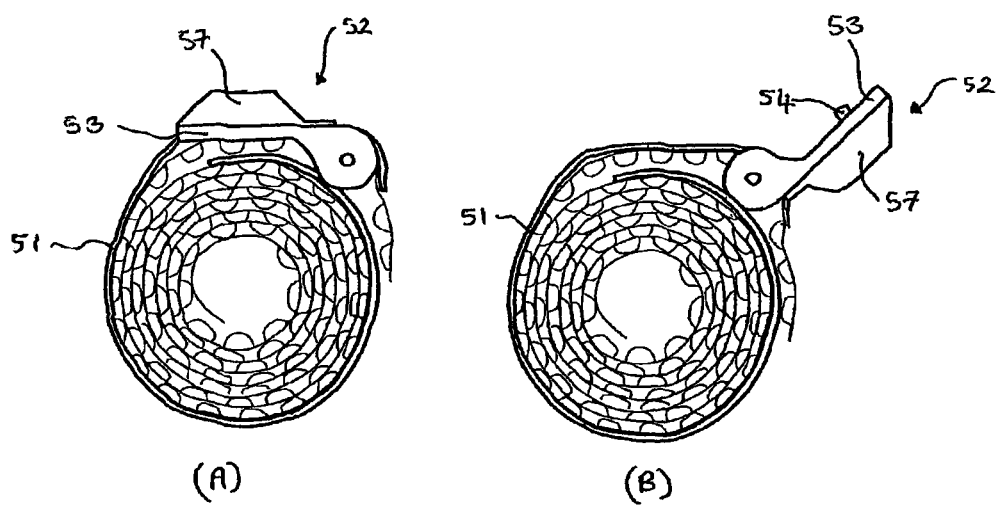
FIGS. 15A and 15B show a side cross-sectional view of the inhaler illustrated in FIGS. 14A and 14B with the actuator in a closed and open position respectively.
Figure 16:
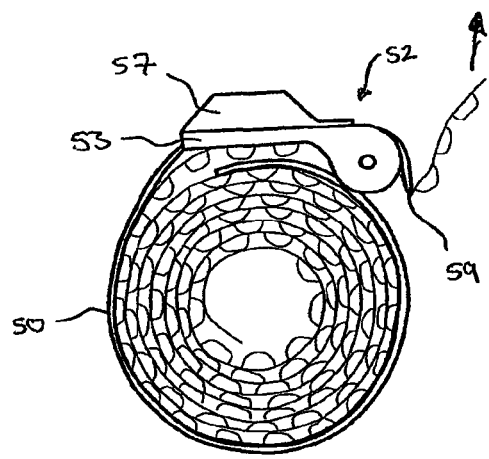
FIG. 16 is another side cross-sectional view of the inhaler shown in FIGS. 14A and 14B.
Figure 17:
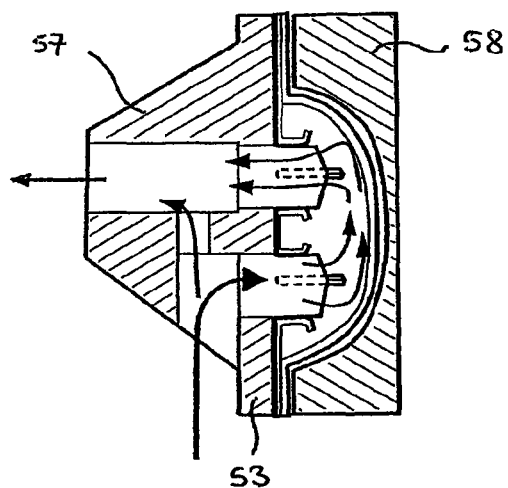
FIG. 17 is a side sectional view of the mouthpiece and actuator during inhalation from a blister.

The indexing wheel 23 is a generally cylindrically shaped member with a set of blister receiving grooves or recesses 24 extending longitudinally along its outer surface parallel to its axis of rotation. Each groove 24 is shaped so as to receive a blister 6a therein as the indexing wheel 23 rotates, as will be explained in more detail below. The recesses 24 are spaced at a pitch which is equal to the distance "d" between the centre lines of a pair of blisters, as indicated in FIG. 13, so that as the indexing wheel 23 rotates, a strip 6 extending through the blister feed path 21 and over the indexing wheel 23 is pulled so that a blister 6a locates in the recess 24 of the indexing wheel 23 situated immediately opposite the aperture 8, as will be explained in more detail below. To enable the indexing wheel 23 to rotate in response to rotation of the actuator 3 in one direction, ratchet teeth 25 are formed on one end face thereof for cooperation with the actuator 3 as will shortly be explained, each tooth 25 comprising an arcuately shaped ramp section 26 and a shoulder 27. The indexing wheel 23 is a close fit in the cylindrical cavity 22 so that the strip 6 is securely held by the indexing wheel 23 and each blister 6a is snugly received and held in the recess 24 opposite the aperture 8 whilst allowing for rotation of the indexing wheel 16 to feed the strip of blisters 6 through the device. As the indexing wheel 23 rotates, the used blisters 6d ate fed out of the cavity 22 down the used blister feed path 30 and through the slot 14 out of the housing 2.

A drive plate 27a depends from a longitudinal edge of the lever arm 7 and carries a drive pawl 28 thereon for cooperation with the ratchet teeth 25 on the indexing wheel 23 during rotation of the actuator 3 from the open to the closed position. The drive pawl 28 is integrally formed in the drive plate 27a by cutting a U-shaped slot therein to form a resiliently deformable tab 29 from which the drive pawl 28 upstands.

The mouthpiece 5 is integrally formed with the lever arm 7 of the actuator 3 and upstands from one side thereof opposite to the side from which the piercing heads 9 extend. The interior of the mouthpiece 5 can be seen from the cross-sectional view of FIG. 9 and is divided into a primary and a secondary chamber 31,32 by a partitioning wall 33. An outside air inlet orifice 34 in the sidewall of the mouthpiece 5 close to where it joins or becomes the lever arm 7 is in communication with the primary chamber 31. The primary chamber 31 is also in communication with one of the apertures 11a in the lever atm 7 that is formed in the vicinity of a piercing head 9. The secondary chamber 32 makes up the main internal volume of the mouthpiece 5 and is in communication with the other aperture 11b in the lever arm 7. A bypass aperture 35 extends through the partitioning wall 33 to communicate the primary chamber 31 with the secondary chamber 32 for reasons that will become apparent.

Figure 7:
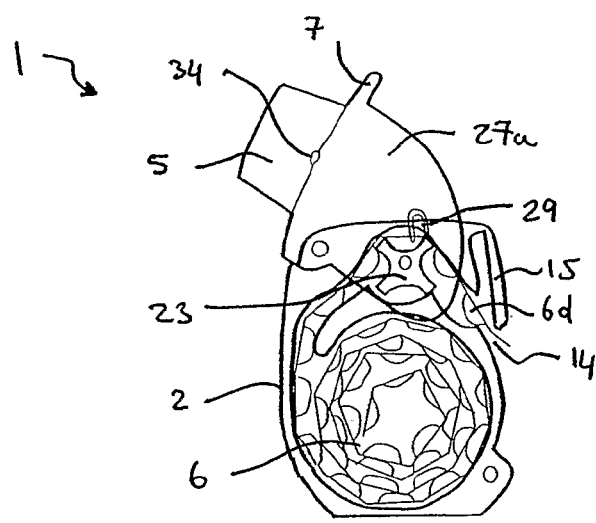
FIG. 7 is a front cross-sectional view of the inhaler illustrated in FIG. 6 in which the actuator is pivotally mounted to the housing.

The path of the blister strip 6 through the device and the way in which it is disposed within the chamber 20 can be most clearly seen in FIG. 7. It will be appreciated that the coils of the blister strip 6 are loosely wound in the chamber 20 so that the blister strip 6 will unwind in response to a pulling force applied to the leading edge 6e of the strip by the indexing wheel 23 as the indexing wheel 23 rotates.

Figure 6:
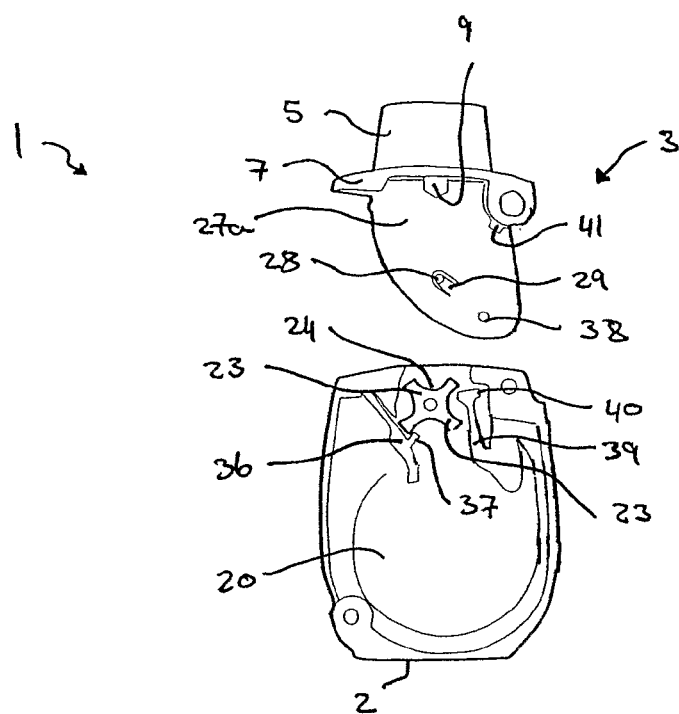
FIG. 6 is a rear cross-sectional view of the inhaler illustrated in FIGS. 1 to 5 with the actuator shown separately.

To prevent rotation of the indexing wheel 23, other than due to rotation of the actuating member 3, the housing 2 is provided with an integrally formed resiliently flexible arm 36 carrying an anti-rotation pawl 37 that normally locates in one of the recesses of the indexing wheel 23 which is not occupied by a blister 6a, as shown in FIG. 6. Engagement of the pawl 37 with the indexing wheel 23 prevents the indexing wheel 23 from rotating. A release pin 38 upstands from the drive plate 27a which engages the arm 37 to push the pawl 38 out of the recess to allow rotation of the indexing wheel 23 when the actuator 3 approaches its fully open position.

When the pawl 38 is deflected from the recess 24, the blister strip 6 could be pulled from the housing 2. To prevent this, a second resiliently deformable anti-rotation pawl 39 is provided on the housing 2. The second anti-rotation pawl 39 has a cam surface 40 thereon which is engaged by a cam member 41 on the actuator 3 when the first anti-rotation pawl 37 is pushed out of the recess 24 of the indexing wheel 23. The second anti-rotation pawl 39 is therefore locked into position and protrudes into another recess 17 of the indexing wheel 23. This prevents the indexing wheel 23 from rotating by more than approximately 45 degrees and so the strip 6 can only be pulled through the device by about half a blister width.

It will be appreciated from the foregoing that the inhalation device according to this embodiment of the invention has a very simple construction with relatively few components. If the cap 4 is integrally formed with the housing 2 in a single moulding and the actuator 3 is formed together with the mouthpiece 5, the piercing heads 9, the drive plate 27a and the drive pawl 28 in another moulding, the device can be formed from as few as 4, 5 or 6 moulded plastic parts.

Operation of the inhaler 1 will now be described. When the inhaler 1 is not in use, the cap 4 and the lever arm 7 are both in a closed position in which the cap 4 covers the mouthpiece 5 and the lever arm 7 lies generally against the side of the housing 2 with the piercing heads 9 extending through the aperture 8 in the housing 2 and into a previously exhausted blister 6d lying immediately below the aperture 8 and constrained in the uppermost recess 24 of the indexing wheel 23 adjacent to the aperture 8. The first and second anti-rotation pawls 37,39 prevent rotation of the indexing wheel 23 in either direction and so locate the blister in position.

When the cap 4 is opened, the lever arm 7 can be pivoted into the position shown in FIG. 3. As the lever arm 7 pivots, the drive pawl 28 on the drive plate 27a rides up the ramp section 26 forming one of the ratchet teeth on the end of the indexing wheel 23 and so no rotation of the indexing wheel 23 occurs. Once a fully open position has been reached, as shown in FIG. 3, the drive pawl 28 has reached the end of the ramp section 26 and drops down against the face of a corresponding shoulder 27 so that as the actuator 3 is rotated back in the opposite direction from the open to the closed position, engagement between the drive pawl 28 and the shoulder 27 causes the indexing wheel 23 to rotate. It will be appreciated that if the lever arm 7 is not opened to its fullest extent before being returned to its closed position, the indexing wheel 23 will not rotate because the drive pawl 28 will not have dropped down to engage a shoulder 27 at the top of the ramp section 26.

Just before the lever arm 7 reaches its fully open position, the release pin 38 on the drive plate 27a engages with the arm 36 from which the first anti-rotation pawl 37 extends and deflects it so that the anti-rotation pawl 37 moves out of the recess 24 in the indexing wheel 23 so that the indexing wheel 23 can rotate and the strip 6 can be indexed when the lever arm 7 is rotated in the opposite direction. At the same time, the cam member 41 engages with the cam surface 40 of the second anti-rotation pawl 39 and locks it into position to ensure that the strip 6 cannot be pulled from the inhaler 1 by more than approximately half the width of a blister 6b.

As the lever arm 7 is pivoted back into its closed position, the indexing wheel 23 is rotated through 90 degrees as a result of engagement between the drive pawl 28 and the shoulder 27 on the indexing wheel 23. Whilst the lever arm 7 is rotated back into its closed position, the anti-rotation pawls 37,39 have returned to their original positions locking the indexing wheel 23 in place. This rotation of the indexing wheel 23 brings the next blister 6b into position immediately below the aperture 8 in the housing 2.

In the final stage of the return stroke of the lever arm 7 back to its closed position, the piercing heads 9 pass through the aperture 8 in the housing 2 and penetrate the lid 6c of the blister 6a that has just been moved into position by the indexing wheel 23. The dose is now ready for inhalation, as will now be described.

Figure 9:
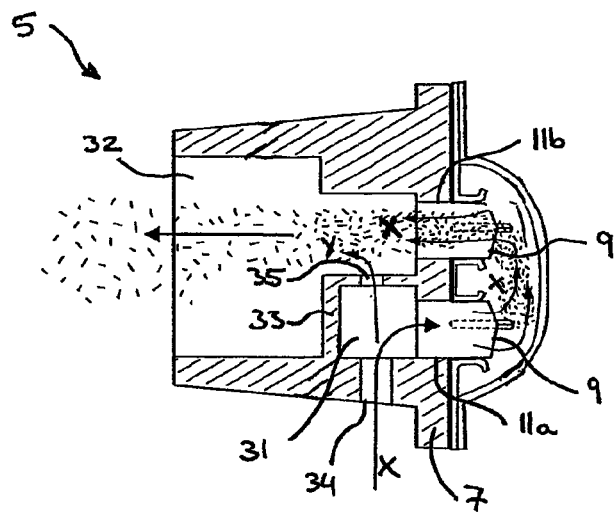
FIG. 9 is a side sectional view of the mouthpiece and actuator during inhalation from a blister.
Figure 10:
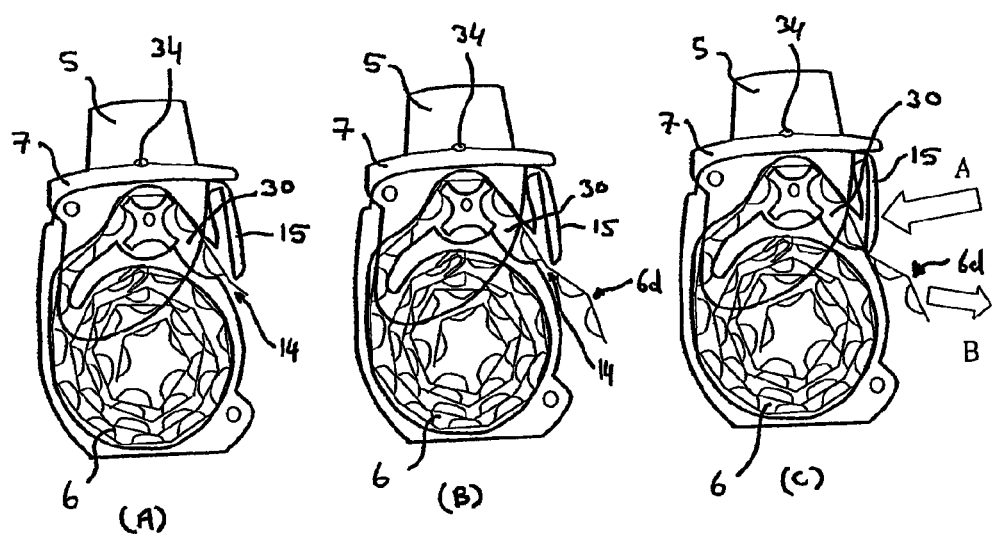
FIG. 10A to 10C show a series of front cross-sectional views of the inhaler according to the invention with a blister strip located therein to show the path of used blisters from the housing.

When a user inhales through the mouthpiece 5, a low pressure region is created in the secondary chamber 32 causes air to be drawn through the blister 6a from the outside air inlet 34 via the primary chamber 31 and the airflow opening 11a in the lever arm 7, as indicated by arrows marked "X" in FIG. 9. This airflow through the blister 6b entrains the dose contained therein, which is carried into the secondary chamber 32 and from there into the patient's airway.

The turbulent airflow generated through the aperture 11b in the lever arm 7 around the piercing element 9 helps to deagglomerate the dose and create a respirable aerosol. The air bypass orifice 35 in the partitioning wall 33 between the primary and secondary chambers 31,32 reduces the overall pressure drop across the device and so makes it easier for the patient to inhale. It also increases turbulence in the secondary chamber 32. In a particularly preferred arrangement, the bypass orifice 35 is situated so that the airflow therethrough, indicated by arrow "Y" in FIG. 9, meets the airflow entering the secondary chamber 32 from the blister at a tangent or right angle so as to create a cyclonic effect or increase the airflow turbulence to assist deagglomeration.

Once the device has been used a number of times, the side cover 13 may be opened and the visible section 6d of used blisters may be detached from those that remain within the device as has already been explained.

Figure 11:
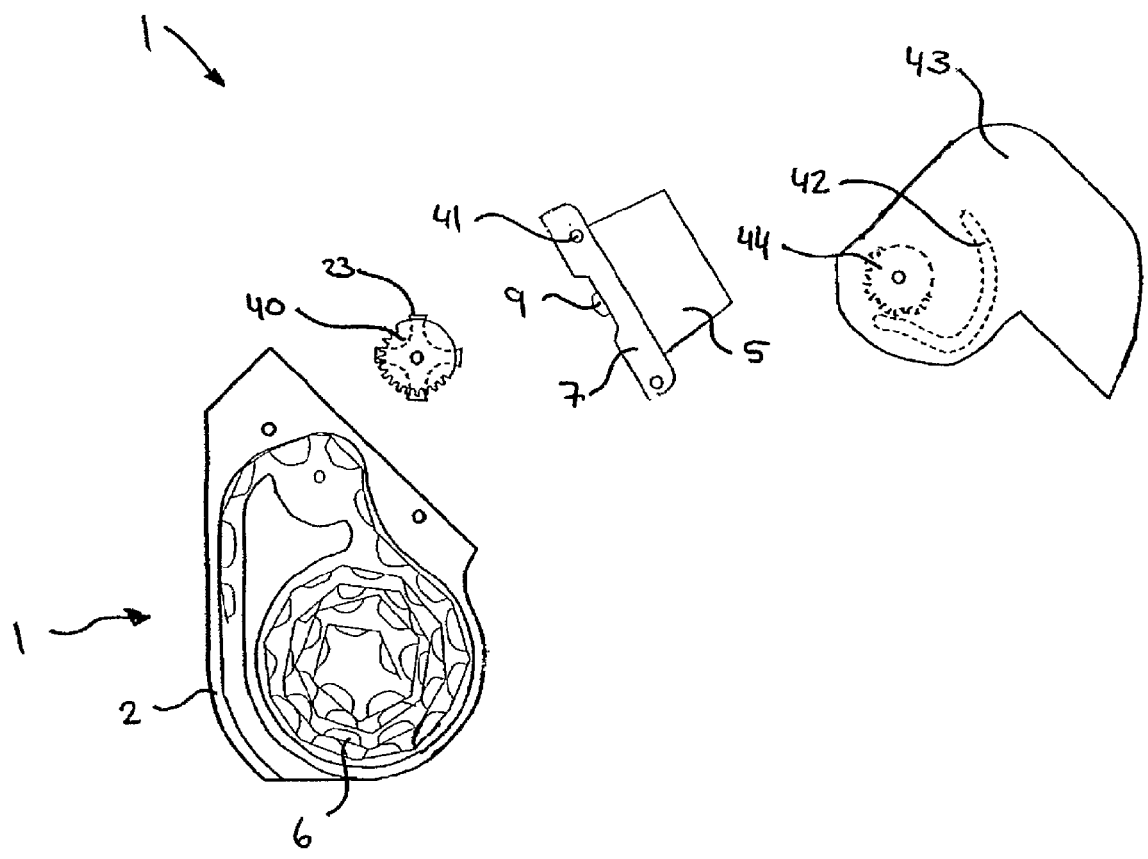
FIG. 11 is an exploded side cross-sectional view of an inhaler according to another embodiment of the invention.
Figure 12:
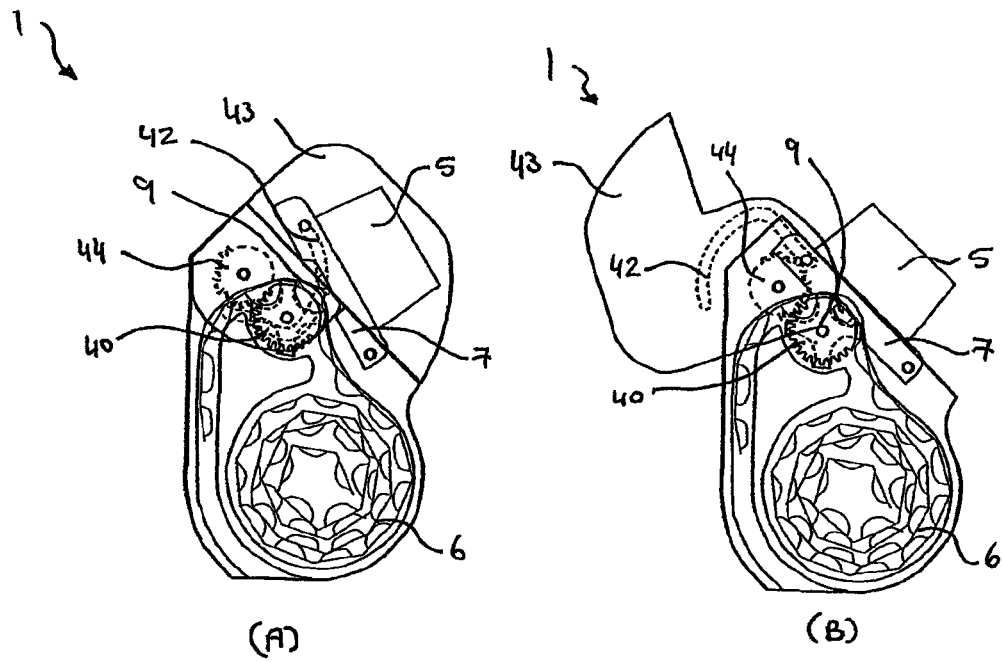
FIGS. 12A and 12B are side cross-sectional views of the inhaler according to the second embodiment with the cap in the closed and open positions respectively.

A second embodiment of the inhaler according to the invention will now be described with particular reference to FIGS. 11 and 12. In this embodiment, the actuator is coupled to the cap covering the mouthpiece so that a blister is pierced when the cap is opened and indexed to move the next unused blister into position beneath the aperture in the housing when the cap is closed. This provides a device that is very simple to operate, as the user does not have to open the cap before pivoting the actuator to index and pierce a blister.

Referring to the exploded view of FIG. 11, the inhaler 1 is similar to the device described with reference to the first embodiment except that the ratchet teeth on the indexing wheel 23 have been replaced with a toothed gearwheel 40 which is attached to the indexing wheel via a one-way or clutch mechanism (not shown) so that the indexing wheel 23 will rotate together with the gearwheel 40 in only one direction of rotation, the gearwheel being free to rotate in the opposite direction relative to the indexing wheel 23.

The actuator has a similar construction to the actuator 3 of the first embodiment and comprises a lever arm 7 with the mouthpiece 5 and piercing heads 9 upstanding from opposite sides thereof. However, in this embodiment, the user does not directly pivot the actuator 3. Instead, a cam pin 41 protrudes from the side of the lever arm 7 adjacent to the remote end opposite the end pivotally mounted to the housing 2. The cam pin 41 is located in a cam track or groove 42 formed on the inside surface of a cap 43 pivotally attached to the side of the housing 2 at the same end but spaced from the location at which the actuator 3 is pivotally attached to the housing 2. The cap 43 also carries a toothed gearwheel 44 attached thereto for rotation together with the cap 43, which lies in meshing engagement with the gearwheel 40 on the indexing wheel 23.

As has already been mentioned with reference to the first embodiment, the inhalation device according to the second embodiment also has a very simple construction with relatively few components. For example, if the gearwheel 44 is integrally formed together with the cap and the actuator 3 is formed together with the mouthpiece 5 and the piercing heads 9, the whole device can be formed from as few as 4, 5 or 6 moulded plastic parts.

Due to the small number of parts and simplicity of the device, there is more storage room within the device for blisters thereby reducing the frequency that it must be refilled or replaced. It is intended that the devices of the present invention will have a capacity to hold between 1 and more than 100 doses although preferably it will be capable of holding between 1 and 60 doses and most preferably between 30 and 60 doses. The payload of each blister may be between 1 μg and 100 mg. However, preferably, the payload is in the region of 1 mg to 50 mg and most preferably between 10 mg and 20 mg. It will also be apparent that due to its simplicity, the device may be disposable once all the blisters contained therein have been used up. In this case, the housing may be formed as a permanently sealed enclosure to prevent tampering.

Operation of the inhaler according to the second embodiment will now be described with particular reference to FIGS. 12A and 12B. As can be seen in FIG. 12A, when the cap 43 is closed, the piercing heads 9 on the actuator 3 are held clear from the aperture 8 in the housing 2 by means of the cam pin 41 located in the cam track 42 in the cap 43. The cam track 42 is preferably shaped so that the cap 43 can be initially pivoted relative to the housing 2 by at least 90 degrees without any movement of the actuator 3 occurring thereby allowing inspection or cleaning of the mouthpiece 5 without piercing of a blister 6a. However, when the cap 43 is rotated relative to the housing 2 beyond 90 degrees, the cam pin 41 is guided by the track 42 causing the actuator 3 to pivot into a position shown in FIG. 12B in which the piercing elements 9 extend through the aperture 8 in the housing 2 and penetrate a blister 6b situated immediately behind the aperture 8 within the housing 2. At this stage, the dose may be inhaled through the mouthpiece 5.

As the cap 43 opens the gearwheel 40 rotates due to engagement with the gearwheel 44 on the cap 43. However, because of the one-way clutch mechanism, the indexing wheel 23 does not rotate as the cap 43 is opened and the gearwheel 40 is rotated in this first direction. However, once the cap 43 is rotated in the opposite direction, i.e. from the open to the closed position following inhalation, drive of the gearwheel 40 is transferred to the indexing wheel 23 so that it rotates and moves the next blister 6a into alignment with the aperture 8. It will be appreciated that during initial movement of the cap 43 from its open to its closed position, the actuator 3 will first be pivoted, due to the engagement of the cam pin 41 in the cam track 42, so that the piercing elements 9 are lifted out of the aperture 8 and back into the position shown in FIG. 12A.

It is envisaged that, in either embodiment, an opening or window could be provided in the housing 2 and a dose number printed on each blister 6a readable through the opening or window so that the user can monitor the number of doses that have been used or that remain in the device. This avoids the need for a complicated dose counting mechanism often found in conventional devices. Alternatively, the housing 2 could be wholly or partially formed from a transparent material so that the number of blisters 6 remaining in the device can clearly be seen through the walls of the housing 2.

As shown in the FIG. 13, the blister strip 6 provided for use with the inhaler 1 of the invention may be provided with serrations, cut-lines 50 or other frangible features to facilitate the separation of the blisters 6a from each other. Alternatively, or in addition to the frangible features, the edge of the blister strip 6 may be provided with notches 51 between each blister 6a to make the strip easier to tear.

Another embodiment of the device will now be described with reference to FIG. 14A to 19. This version of the device has the particular benefit of being small in size relative to the number of blisters that it may contain. Instead of placing the indexing wheel in its own cavity adjacent to the aperture in the housing through which the piercing heads extend, the indexing wheel is formed integrally with the hinge, which pivotally connects the actuating lever to the housing. This frees up more space within the housing for blister storage. As can be seen from the drawings, the device is able to contain a coil of at least 60 blisters.

Referring first to FIGS. 14A and 14B, there is shown two perspective views of the inhaler according to this embodiment. The inhaler 50 is similar to the inhaler 1 of the first embodiment and comprises a housing 51 having an actuator 52 in the form of a lever arm 53 pivotally mounted to the housing 51 at one end. A piercing member comprises a pair of piercing heads 54 that extend from the lever arm 53 and locate in an aperture 55 in the housing when the actuator 52 is in a closed position with the lever arm 53 lying substantially against the housing 51, as shown in FIG. 14A. A cap 56 is pivotally attached to the housing 51 and is operable to cover the mouthpiece 57 when the inhaler is not in use.

As with the first and second embodiments, the mouthpiece 57 is integral with the lever arm 53 although it has a triangular or semicircular section against which the lips can be placed, as opposed to a tubular section which is placed in the mouth. The shape of the mouthpiece and the airway construction within it is illustrated in the cross-sectional view of FIG. 18. It will be appreciated that the airway construction is very similar to the construction of the airway described with reference to the first and second embodiments and so no further description of it will be made here. However, it will be appreciated that because the indexing wheel is now located away from the region where the blister is pierced, the blister to be pierced is now supported in a blister support block 58 (see FIG. 17).

The device 50 includes an indexing wheel (not shown) incorporating a ratchet mechanism as has already been described with reference to the first and second embodiments, except that in this embodiment the indexing wheel has been made integral with the hinge about which the lever arm 53 pivots so that it rotates about the same axis as the lever arm 53.

When the cap 56 has been opened and the lever is pivoted from its closed position (as shown in FIG. 14A) into its open position (as shown in FIG. 14B), the indexing wheel rotates together with the lever due to engagement between a ratchet mechanism between the indexing wheel and the lever 53 and so draws a blister into alignment with the aperture 55 and locates in the blister support block 58. However, when the lever is returned to its closed position, the indexing wheel does not rotate due to the ratchet mechanism so the blister strip remains stationary. A second ratchet connection between the indexing wheel and the housing prevents backwards rotation the indexing wheel. During the final part of the return stroke, the piercing elements 54 extend through the aperture 55 and pierce the lid of the aligned blister. The dose is now ready for inhalation through the mouthpiece 57.

As described with reference to the previous embodiments, the device may incorporate a chamber to receive used blisters. However, this is not essential and the used blisters may simply be fed out of the device. A cutting edge 59 (see FIG. 16) may extend from the aperture against which used blisters may be torn off by pulling them against the edge in the direction indicated by the arrow in the drawing. The cutting edge may be serrated to facilitate detachment. It will be noted that the strip is prevented from being pulled out of the device by the piercing heads, which are located in a blister, and secures it in position.

It will be appreciated that any configuration of piercing member may be used including solid or hollow pins as well as piercing blades. However, it is desirable to include features that enhance the flow of air into the blister to aid entrainment and deagglomeration by, for example, introducing a swirling airflow into the blister. One particular arrangement of piercing head 60 which may be employed with any embodiment of the invention and which allows a freer flow of air into the blister will now be described with reference to FIGS. 18 and 19.

Figure 18:
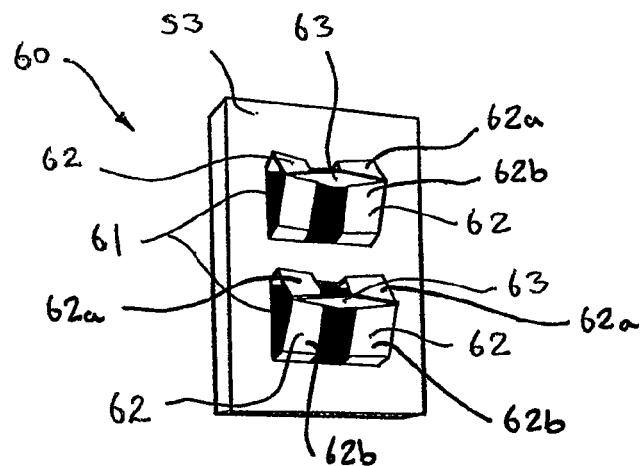
FIG. 18 shows an alternative configuration of piercing elements on the actuator according to any embodiment of the invention.

As can be seen from FIG. 18, the piercing member 60 is preferably integral with the lever arm that has a pair of apertures 61 therein for the flow of air into the blister and the flow of air together with the dose out of the blister. The piercing member 60 comprises a pair of piercing heads each of which comprises a pair of secondary cutting elements 62 spaced from each other and extending in a lateral direction from a pointed primary cutting element 63 which is mounted on and extends between the secondary cutting elements 62. The primary and secondary cutting elements 62,63 extend over one of the apertures 61 in the lever arm 53.

Figure 19A:
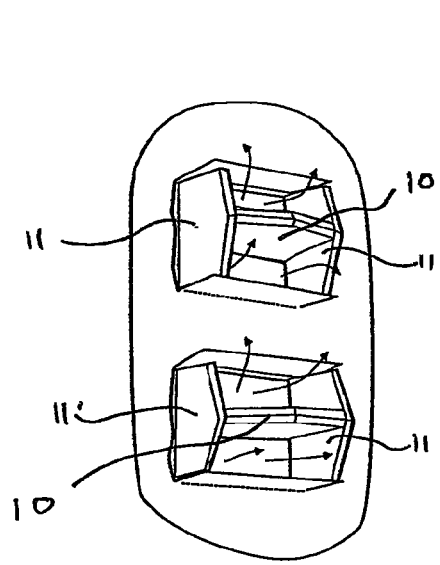
FIG. 19A shows the airflow into the blister using the piercing elements of FIG. 8A
Figure 19B:
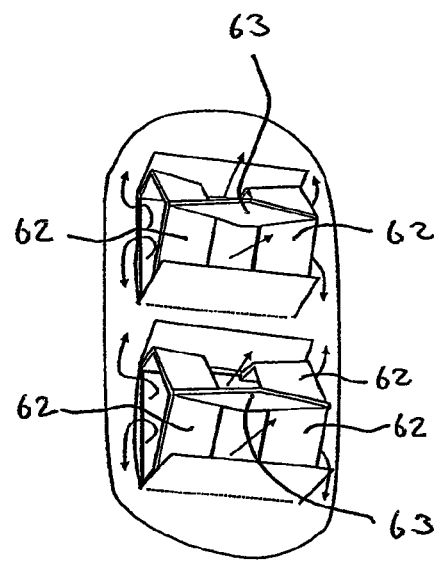
FIG. 19B shows the airflow into the blister using the piercing element of FIG. 18.

Each of the secondary cutting elements 62 divided into first and second cutting members 62*a*, 62*b* that extend laterally from opposite sides of the primary cutting element 63. The first and second cutting members 62*a*, 62*b* are upwardly angled away from the lever arm and the primary cutting element upstands from the secondary cutting member 62 at the point where the first and second cutting members 62*a*,62*b* of each secondary cutting element 62 meet. The secondary cutting elements 62 incline inwardly toward each other so that the central piercing member 63 has diamond shape in side profile. As shown in FIG. 19B, this open construction allows more air to flow around the sides of the blister in comparison with the piercing member arrangement of FIG. 8A, as the side teeth restrict airflow into the blister (as shown in FIG. 19A).

It will be appreciated that the dimensions of the piercer of the present invention can be chosen to suit different sizes and shapes of blisters. Furthermore the number and arrangement of piercers can be varied within the scope of the invention. For example, a large blister may have a pair of larger piercers, or multiple pairs of smaller piercers, for example two piercers for the air inlet and two for the air outlet.

It will be further appreciated that the use of the piercer of this invention is not limited to the inhalers described in the embodiments and may be used with any inhaler comprising a puncturable blister.

Referring to FIGS. 20 to 26, there is shown another embodiment of the invention that will now be described in detail.

Figure 20:
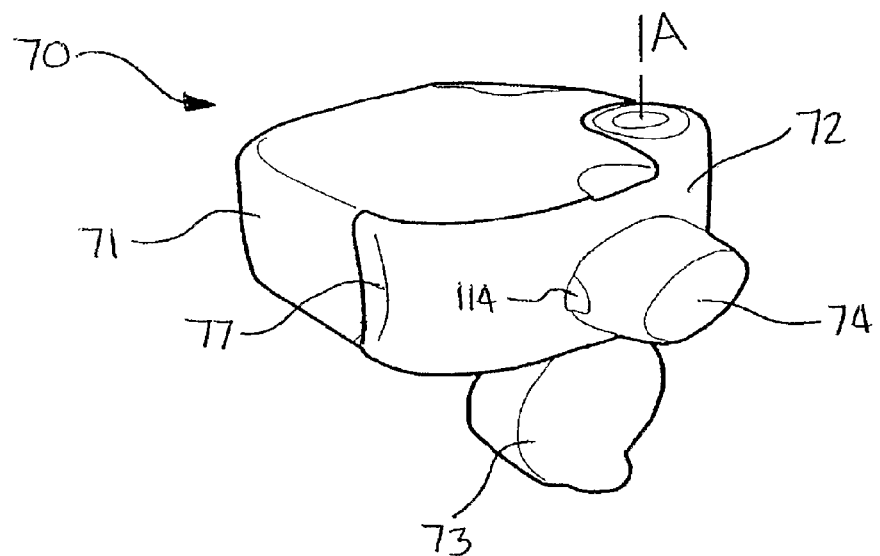
FIG. 20 illustrates a perspective view of another embodiment of inhaler according to the present invention with the cap open and the actuator in the closed position in which it lies against the housing of the inhaler.
Figure 21:
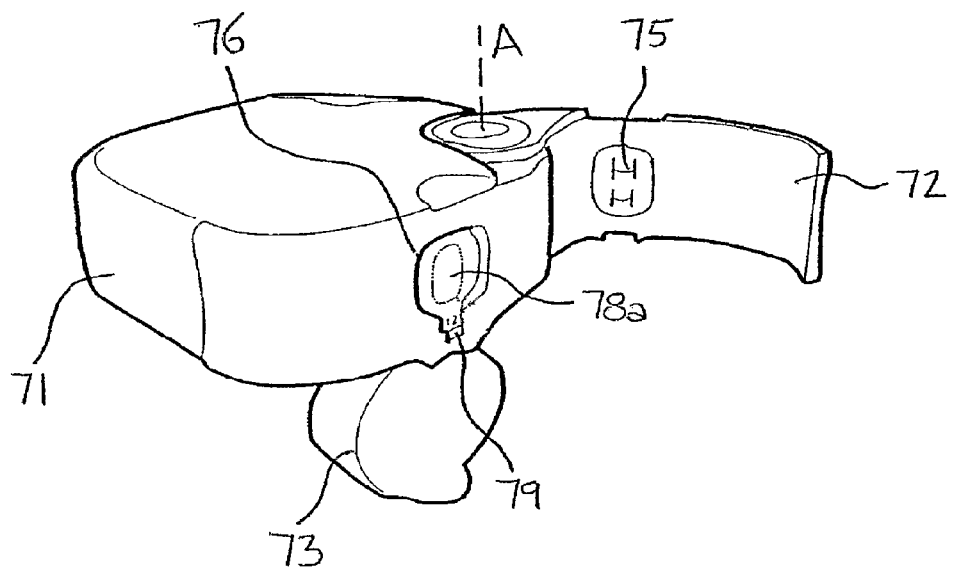
FIG. 21 illustrates a perspective view of the inhaler shown in FIG. 20 but after the actuator has been pivoted with respect to the body into an open position.
Figure 22:
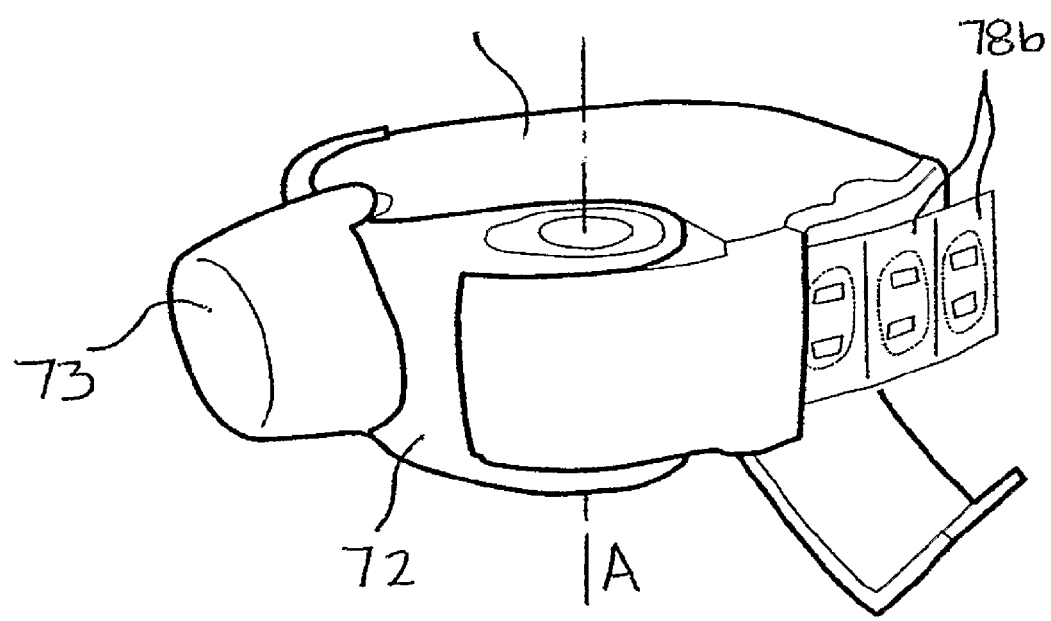
FIG. 22 illustrates another perspective view of the inhaler shown in FIGS. 20 and 21 with a strip of used blisters protruding from the housing and a used blister door in an open position.

The inhaler 70, according to this embodiment, comprises a housing 71 having an actuator 72 pivotally mounted thereto for rotation relative to the housing 71 about an axis indicated by the line marked "A" in FIGS. 20 to 22. A cap 73 is pivotally attached to the housing 71 and may be moved between an open position, as shown in FIG. 20, and a closed position in which the cap 73 covers a mouthpiece 74 to protect it and to prevent the ingress of dirt into the housing 71 through the mouthpiece 74.

In FIG. 21, the actuator 72 has been pivoted about axis "A" from its closed position shown in FIG. 20 into its fully open position to reveal a piercing member, comprising a pair of piercing heads 75, upstanding from the actuator 72 and an aperture 76 in the housing 71 through which the piercing heads 75 extends when the actuator 72 is in its closed position. A finger grip 77 is integrally moulded into the front lip of the actuator 72 to facilitate movement of the actuator 72 by the user between its open and closed positions.

As with the previous embodiments, the housing 71 contains a coiled strip of blisters 78 (see FIG. 23) and one such blister 78*a* (see FIG. 21) is located in a piercing position in which it is visible through the aperture 76. It will be noted that each of the blisters in the strip 78 are numbered and the number of the blister located in a piercing position is also visible through the aperture 76. One edge of the aperture 76 is provided with a cutout 79 (see FIG. 21) to enable the number of this blister 78*a* to be seen by the user when the actuator 72 is in its open position.

As has already been described with reference to the embodiment of FIG. 4, a cover 80 is pivotally attached to the housing 71 and encloses a space to receive used blisters 78*b* that are fed into this space through a slot 81 (see FIG. 23) formed in the wall of the housing 71. It will be appreciated that the space enclosed by the cover 80 is sufficiently large enough to accommodate only a few used blisters 78*b* at a time and so a section of used blisters 78*b* must periodically be removed from those unused blisters 78 that remain in the housing 71. In this embodiment, as shown in FIG. 22, the cover 80 is pivotally hinged to the housing 71 for rotation about an axis which is substantially parallel to the direction of movement of used blisters 78b out of the housing 71. Even when the cover 80 is closed, there is a gap (not shown) between the cover 80 and the housing 71 so that, if a user does not remove a strip of used blisters 78b when the space is full, the used blisters 78b will pass through this gap and protrude out of the housing 71.

Figure 23:
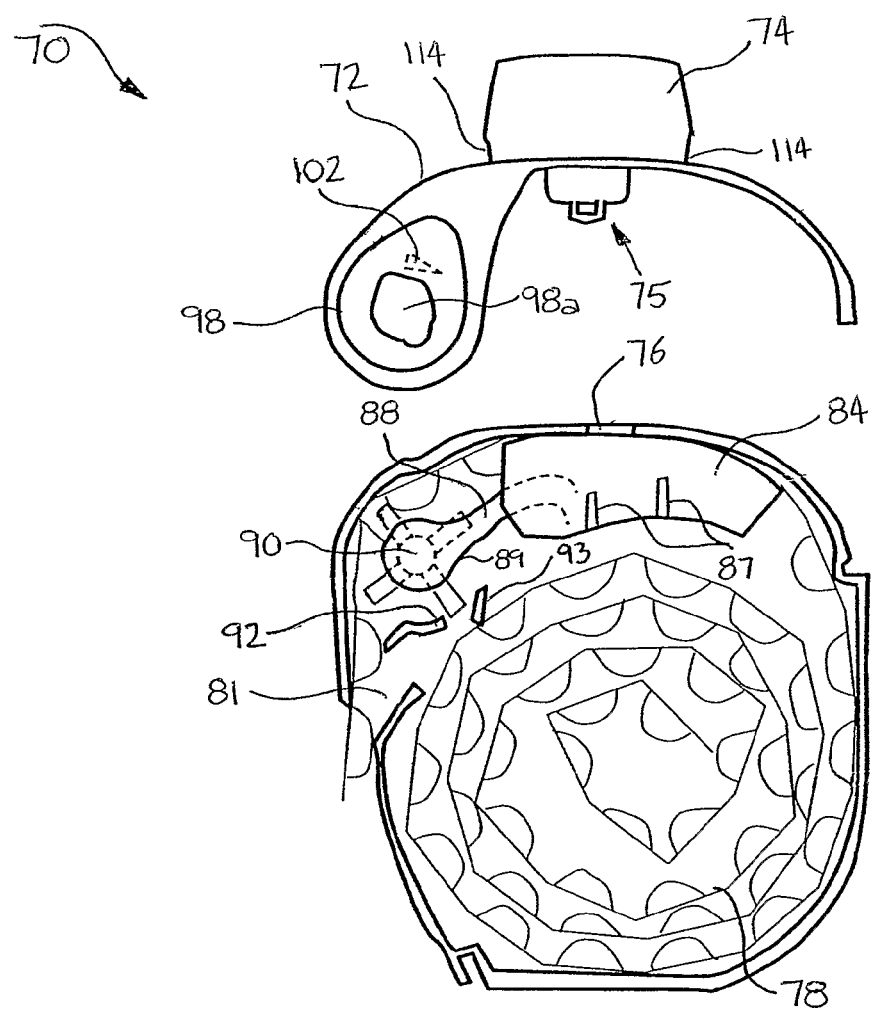
FIG. 23 illustrates a side view of the inhaler shown in FIGS. 20 to 22 with one half of the housing omitted so that the internal components are visible together with a coiled strip of blisters located in the housing, the actuator is shown detached from the housing and the used blister cover is omitted altogether for clarity.
Figure 24:
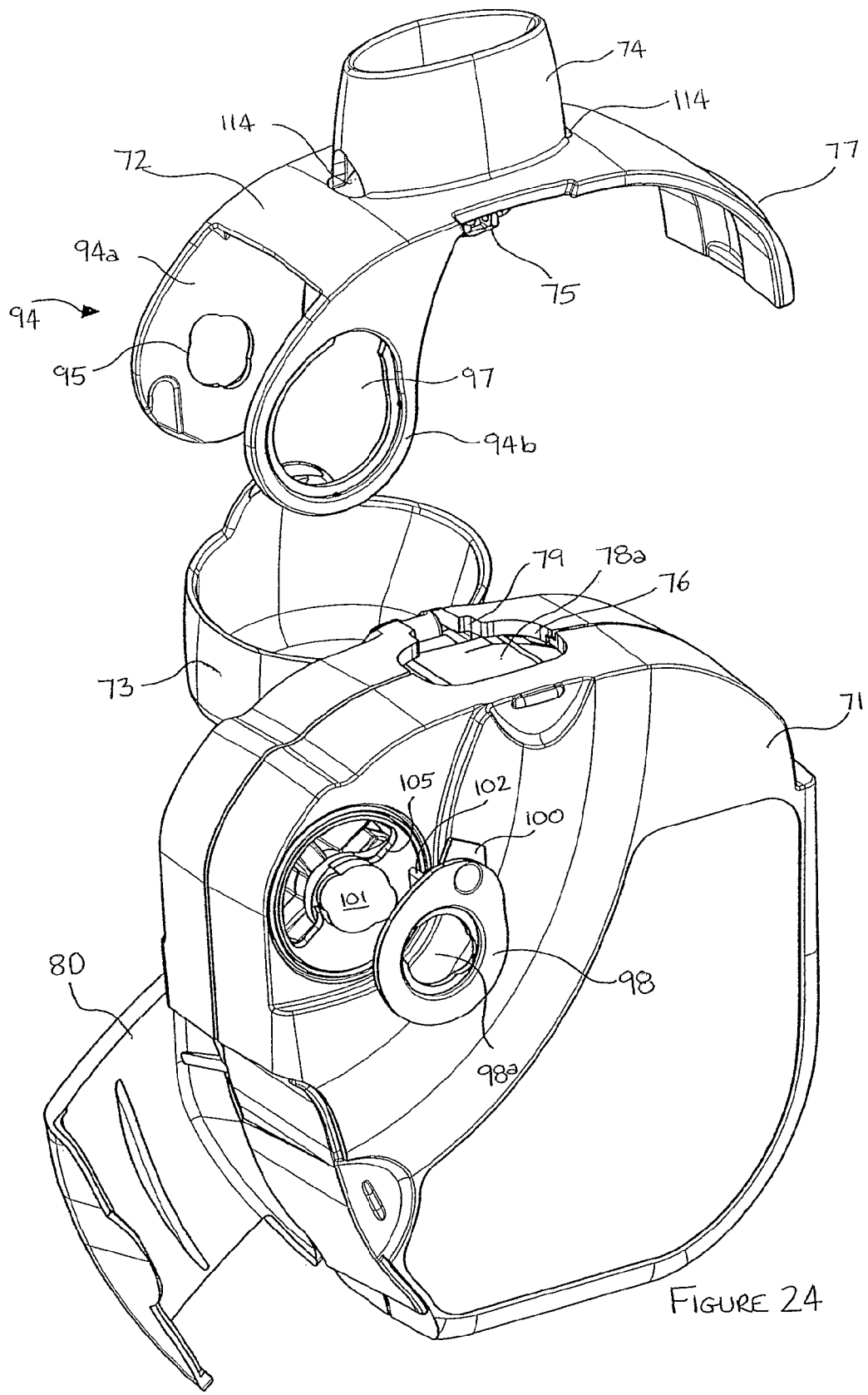
FIG. 24 illustrates a partially exploded perspective view of the inhaler shown in FIGS. 20 to 23.
Figure 25:
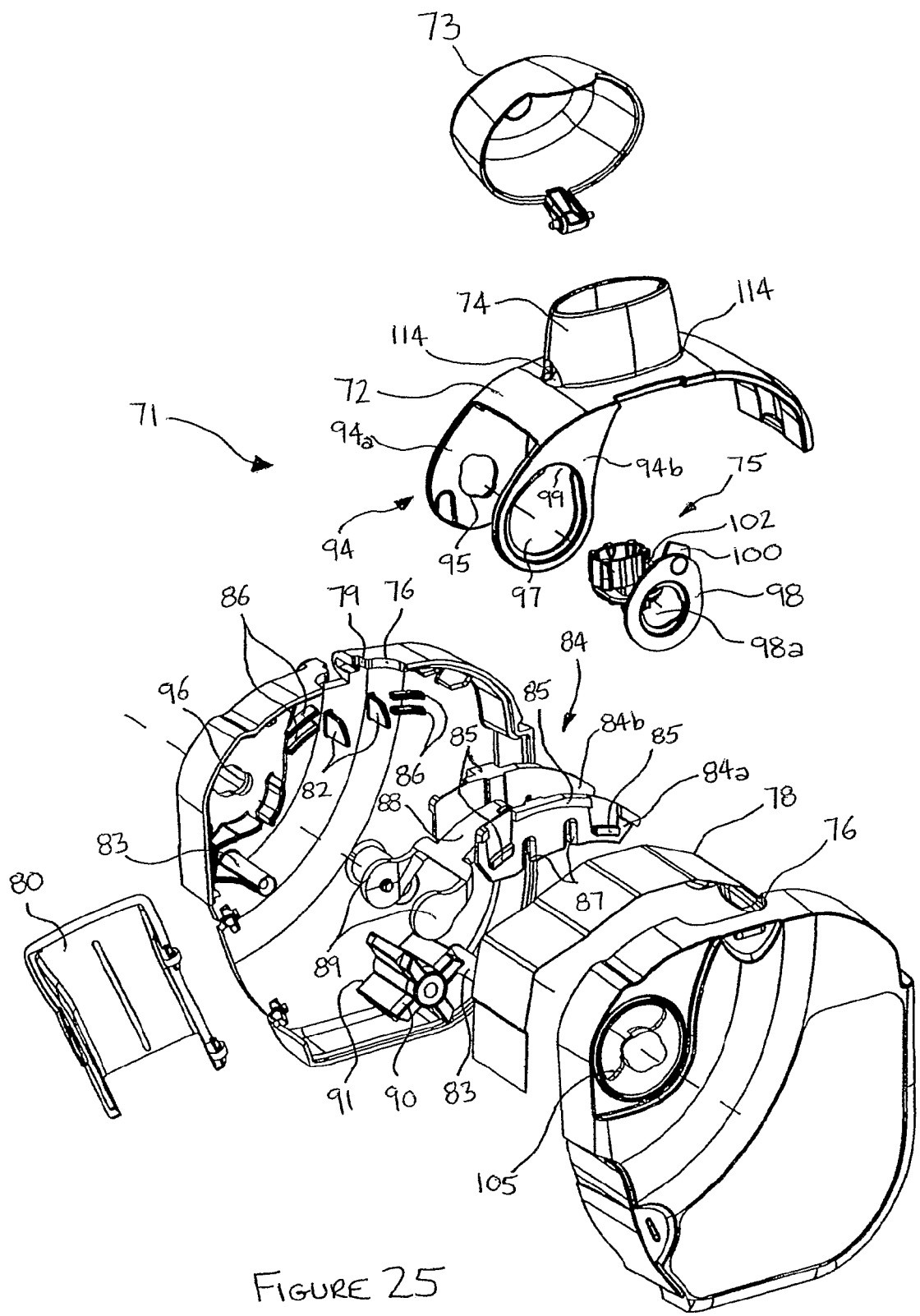
FIG. 25 illustrates a fully exploded perspective view of the inhaler shown in FIG. 24.

As can be seen from FIGS. 23 and 25, the housing 71 is preferably formed in two halves which, as with all the embodiments, may be formed from a translucent plastic such as polypropylene and which are held together using suitably positioned and integrally moulded clip-in mounting pins (not shown) that cooperate with corresponding mounting posts 83. In the side view of the device shown in FIG. 23, one half of the housing 71 has been removed so that the location and path of a coiled strip of blisters 78 through the housing 71 is clearly visible, as are the internal components of the device. The mouthpiece cap 73 and the cover 80 have been omitted from FIG. 23 for the purposes of clarity.

Although the two casing halves may be separable by the user to enable them to refill the housing with a fresh strip of blisters, it is also envisaged that the inhaler could be of the "single use" type in which a strip of blisters is located in the housing during assembly, which is then subsequently sealed. Once that strip of blisters has been exhausted, the whole device is simply thrown away. It will be appreciated that the simplicity of the preferred embodiments of the device and the fact that they are made from a relatively small number of components (no more than nine), all of which are made from a plastics material, means that it is very cheap to manufacture and so rendering it disposable after a single strip of blisters has been exhausted is a viable proposition. Sealing the housing during manufacture also renders the device tamperproof.

The blister strip 78 passes over a blister strip locator chassis 84 received in the housing 71 and mounted adjacent to the aperture 76. As can be most clearly seen from the exploded view of FIG. 25, the chassis 84 comprises two arcuately shaped parallel wall members 84a, 84b joined to and spaced from each other by a width which is only slightly greater than the width of the blister strip 78 so that the strip 78 (only a short section of which is shown in FIG. 25) passes between the wall members 84a, 84b and is guided and supported by them and by the upper wall of the housing 71 as the strip 78 passes therethrough. Each wall member 84a, 84b is provided with integrally moulded lugs 85 that locate between corresponding lugs 86 integrally moulded into the housing 71. Similarly, each wall member 84a, 84b has slots 87 which mate with corresponding locating features 82 on the housing 71 to firmly mount the strip locator chassis 84 in position.

The strip locator chassis 84 includes a resiliently deformable arm 88 depending from between the wall members 84a, 84b. The arm 88 is preferably integrally moulded together with the strip locator chassis 84 from a plastic material such as acetal. The free end of the arm 88 is divided into two forks 89 between which an indexing wheel 90 is rotatably mounted.

Figure 26:
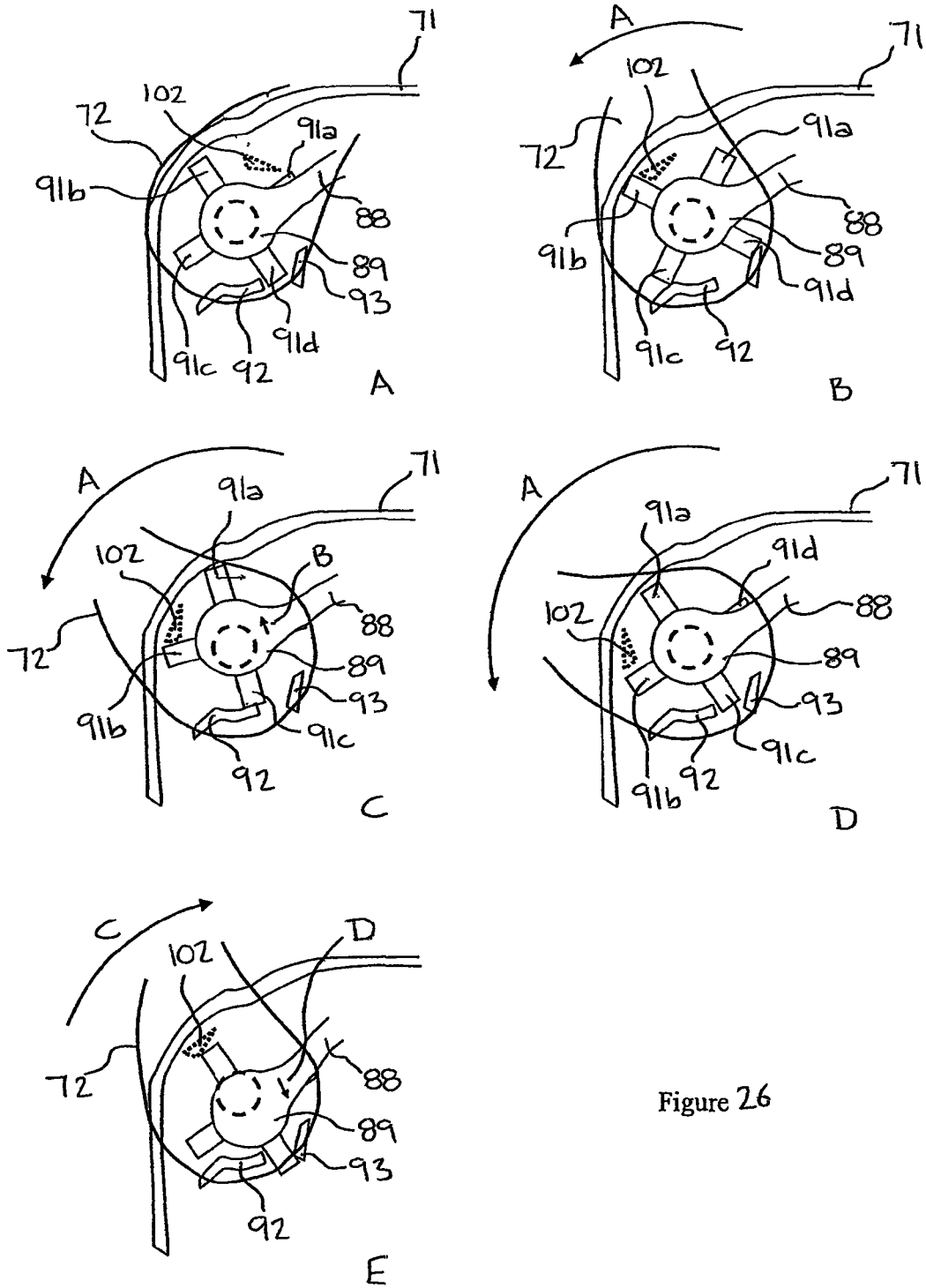
FIG. 26A to 26E each illustrate an enlarged portion of the inhaler shown in FIG. 23 and show the various positions of the indexing wheel during operation of the device.

Referring now to FIG. 26, the indexing wheel 90 has four spokes 91 arranged in an "X" shape and it is positioned substantially coaxial with the axis "A" about which the actuator 72 rotates with respect to the housing 71. The housing 71 is also provided with indexing wheel anti-rotation and location ramps 92,93 which the indexing wheel 90 interacts with to selectively prevent and permit rotation of the indexing wheel 90, as will be explained in more detail later.

The actuator 72 includes a pair of flanges 94a,94b. One flange 94a has a shaped opening 95 that locates directly on a correspondingly shaped spigot 96 integrally formed on one-half of the housing 71. The other flange 94b is provided with a larger opening 97 that is shaped to receive a coupling plate 98 therein. The flange 94b is provided with a recess 99 in the edge of the opening 97 in which is received a locating tab 100 protruding from the coupling plate 98. The coupling plate 98 has a shaped opening 98a that locates on a correspondingly shaped spigot 101 on the other half of the housing 71. An arcuately shaped opening 105 in the housing 71 surrounds the spigot 101 through which extends an angularly shaped drive tooth 102, which protrudes inwardly from the coupling plate 98. The drive tooth 102 extends into a space between two spokes 91 of the indexing wheel 90 and its function will now be described with reference to FIG. 26.

FIG. 26 illustrates a series of drawings to show how the indexing mechanism works when the actuator 72 is rotated between its closed and open position and back to its closed position once again. The blister strip 78 has been omitted from FIG. 26 for clarity although it will be apparent that, as the indexing wheel 90 rotates, a blister will be located between a pair of spokes 91 and pulled through the housing 71.

Referring to FIG. 26A, the actuator 71 is in its closed position and the arm 88, with the indexing wheel mounted thereto, lies in an unstressed or relaxed state in which no external forces are applied to it. The drive tooth 102 can be seen positioned between two of the spokes 91a, 91b and spoke 91d is positioned between the anti-rotation and location ramps 92,93. The anti-rotation ramp 92 prevents any rotation of the indexing wheel 90 in a clockwise direction as viewed in the drawing.

When the actuator 71 is rotated towards its open position, in the direction of arrow "A" in FIG. 26B, the drive tooth 102 contacts spoke 91b. Further rotation of the actuator 71, as shown in FIG. 26C, causes the indexing wheel 90 to rotate, in an anti-clockwise direction as viewed in the drawing, due to the engagement between the drive tooth 102 and the spoke 91b, thereby indexing the blister strip 78.

As the indexing wheel 90 rotates, spoke 91c comes into contact with the anti-rotation ramp 92. When the anti-rotation ramp 92 and the spoke 91c engage, further rotation of the actuator 71 in the direction of arrow marked "A" causes the arm 88 to resiliently deform and deflect in an upward direction (in the direction of the arrow marked "B" in FIG. 26C) so that the spoke 91c can clear the anti-rotation ramp 92. When the actuator 71 has been rotated into its fully open position, the indexing wheel 90 has rotated through a full 90 degrees and spoke 91c clears the anti-rotation ramp 92 thereby allowing the indexing wheel 90 to drop back down and the arm 88 to return to its original undeformed state.

The actuator 71 is now rotated back into its closed position, in the direction of arrow "C" in FIG. 26E. The drive tooth 102 is shaped so that, on the return stroke of the actuator 71, it slides over the top of the preceding spoke 91a and does not rotate the indexing wheel 90 in a clockwise direction. As shown in FIG. 26E, engagement of the drive tooth 102 with the indexing wheel 90 actually causes the arm 88 and the indexing wheel 90 to deflect downwardly in the direction of arrow marked "D" in FIG. 26E. In this position, spoke 91c is pushed down in between the anti-rotation and location ramps 92,93 thereby preventing any rotation of the indexing wheel 90 in either direction.

At the completion of the return stroke, the piercing heads 75 pierce a previously unused blister that has just been indexed into place and is visible through the aperture 76 in the housing 71.

It will be appreciated that, if the actuator 71 is returned to is closed position before the full stroke is completed, the tooth 102 will engage the spoke 91a and cause the indexing wheel 90 to rotate in a clockwise direction back into its original position. This ensures that a partial index cannot take place and so the piercing heads 75 will always enter a blister.

Figure 27:
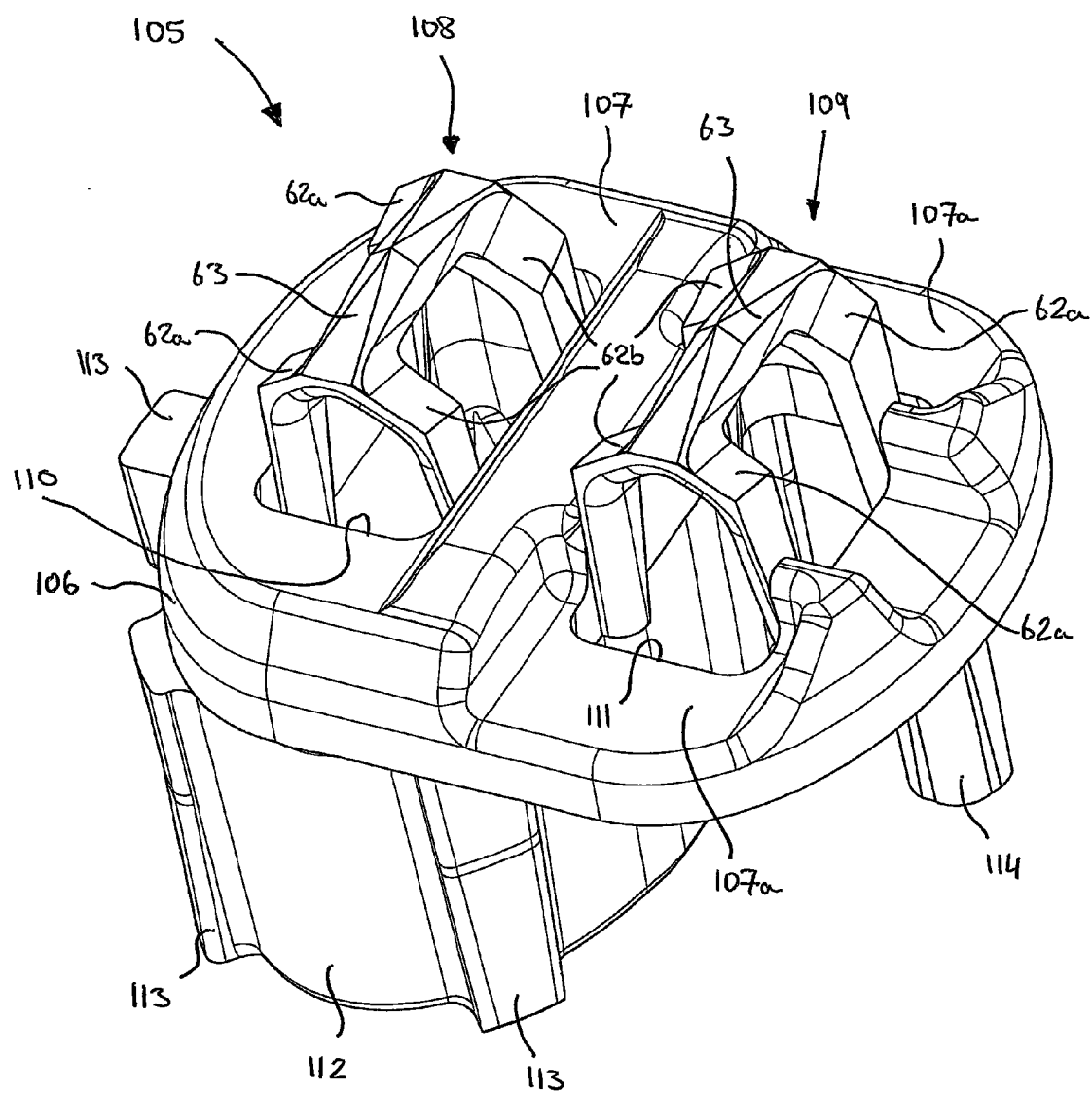
FIG. 27 illustrates a perspective view of a piercing head module primarily intended for use with the embodiment described with reference to FIGS. 20 to 27 but which may also be used with any of the previously illustrated embodiments.
Figure 27A:
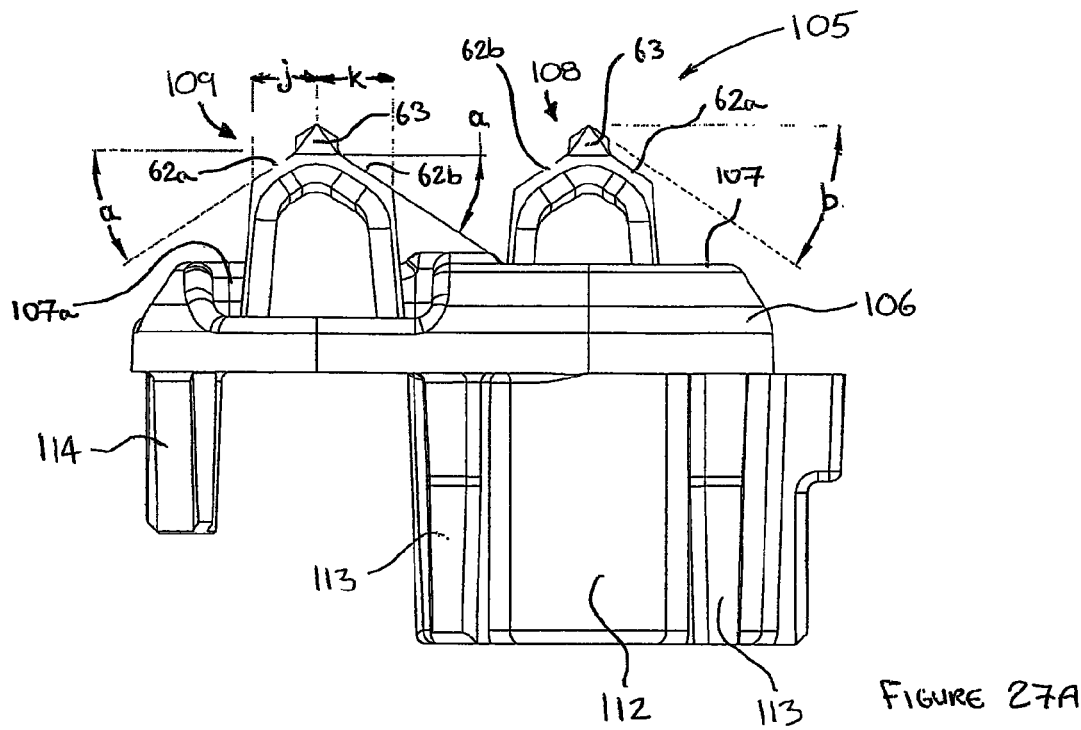
FIG. 27A illustrates a side view of the piercing head module shown in FIG. 27.
Figure 27B:
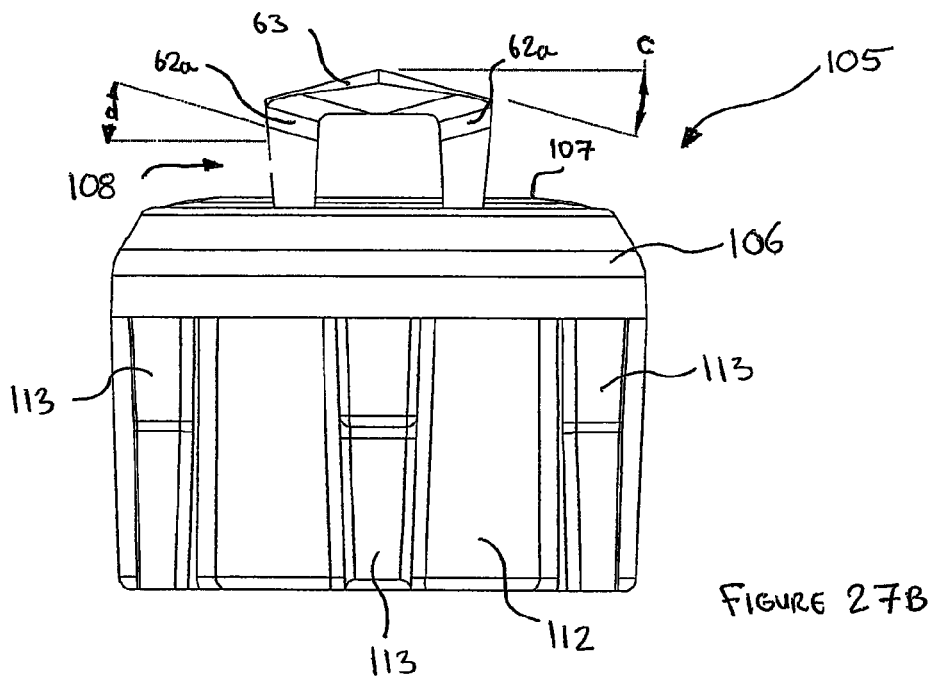
FIG. 27B illustrates an end view of the piercing head module shown in FIGS. 27 and 27A.
Figure 28:
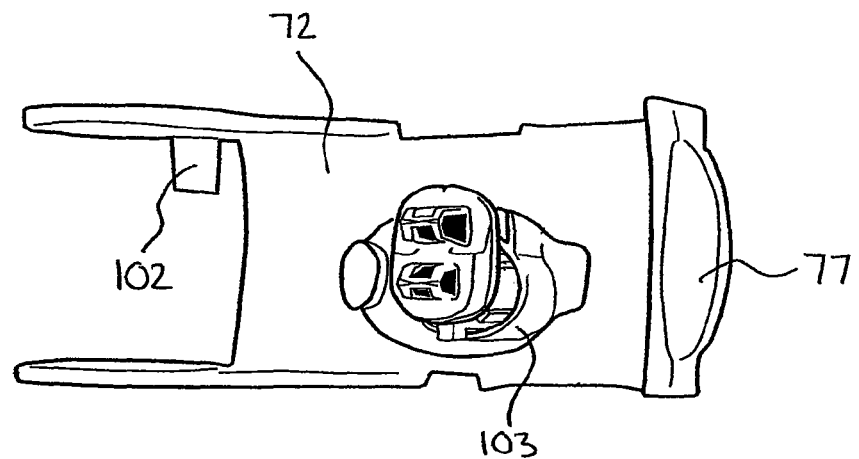
FIG. 28 illustrates a perspective view of the actuator used with the embodiment shown in FIGS. 20 to 26 with the piercing head module of FIG. 27 mounted thereto.

Although the piercing heads 75 may be integrally formed together with the actuator 71, it is also envisaged that the piercing member may be formed as a separately moulded component 105, as shown in FIGS. 27, 27A and 27B, which locates in a walled recess 103 in the actuator 72, as shown in FIG. 28. The piercing heads then extend from this separately moulded component. This will now be described in more detail.

The piercing member 105 may be used with any of the embodiments of the inhalation device described herein and, as shown in FIGS. 27, 27A and 27B, comprises a main body portion 106 having an upper surface 107 which lies flush against the upper surface of a lid of a pierced blister 119 when the piercer has fully entered the blister 119. The piercing heads comprise one piercing tooth 108 upstanding from the upper surface 107 and another piercing tooth 109 upstanding from a relieved or recessed region 107a of the upper surface 107. The geometry of teeth 108,109 is similar to the geometry of the teeth already described with reference to FIGS. 18 and 19. Apertures 110,111 are formed in the upper surface 107 and recessed region 107a beneath teeth 108,109 respectively.

As can be seen in FIGS. 27A and 27B, the angles of the piercer are chosen to facilitate effective and clean cutting of the foil without tearing the foil in an uncontrolled manner. The preferred ranges and values for these angles are given in the table below:

| Angle | Preferred range | Value of embodiment of FIGS. 27, 27A, 27B |
|---|---|---|
| a | 15°-45° | 33° |
| b | 15°-45° | 34° |
| c | 5°-30° | 15° |
| d | 5°-30° | 16° |

It may be advantageous to form the primary cutting element 63 so that it is positioned asymmetrically with respect to the secondary cutting elements 62. The first and second cutting members 62a,62b of each secondary cutting element 62 each extend laterally from the primary piercing element by different distances such that the two flaps formed by a piercing head are not the same size, as can be seen in FIG. 27A. As shown in the drawing the piercing heads 108,109 are arranged so that smaller flaps are formed towards the ends of the blister's major axis where the depth of the blister is shallower, and longer flaps are formed towards the centre of the blister where the blister is deeper. The relative length of the first and second cutting members 62a,62b is defined by the ratio k:j in FIG. 27A. Preferably this ratio is between 1 and 2. In the embodiment of FIGS. 27, 27A and 27B the ratio is 1.2. By making the flaps unequal sizes, agglomerates of medicament are less likely to get trapped within the blister.

A short tubular section 112 depends from the other side of the main body portion 106 in the opposite direction to the tooth 108 and is in communication with the aperture 110. The outer surface of the tubular section 112 has axially extending spacer ridges 113 for reasons that will become apparent. A mounting pin 114 also depends from the main body portion 106 to facilitate attachment of the piercing member 105 to the actuator 72.

When a user inhales through the mouthpiece 74, air is sucked through aperture 111 and into the blister 119 via an opening in the lid 119a of the blister 119 created by tooth 109. Tooth 109 upstands from a recessed region of the main body portion 106 so that a gap is created between the blister lid 119a and the surface of the recessed region 107a to allow free and unrestricted flow of air into the blister 119 through the aperture 109. The drug 119c contained in the blister 119 is entrained in the airflow entering the blister 119 formed by tooth 109 and is carried out of the blister 119 through the opening cut by tooth 108 through the aperture 110 and tubular section 112 into the mouthpiece 74 from where it passes into the patient's airway. The upper surface 107, around tooth 108 is shaped to fit closely against the blister lid when the teeth 108,109 have entered the blister 119 to their fullest extent so that leakage of air into the exit airflow between the upper surface 107 and the blister lid 119a is minimised.

As already described with reference to FIG. 9, to reduce the overall pressure drop across the device and make it easier for the patient to inhale a dose, outside air is introduced into the exit airflow through a bypass conduit 118. In this embodiment, the piercing head 105 is mounted to the actuator 72 via the tubular section 112 that locates within the walled recess 103. The ridges 113 form an interference fit with the walled recess 103 but gaps or spaces between the ridges 113 form a bypass conduit 118 through which bypass air is drawn into the mouthpiece 74 together with the airflow passing through the blister 119. It will be appreciated that the bypass air does not pass through the blister 119 but enters the mouthpiece 74 separately. This reduces the overall resistance to inspiratory flow, making the device easier to use. As has been described with reference to the embodiment of FIG. 9, mixing of bypass air with air that has passed through the blister 119 also enables more efficient dispersion of drug in the inspired air. A mesh 115 (see FIG. 29) may also be moulded into the mouthpiece 74 through which all the inspired air passes so as to provide additional dispersion.

Holes 114 are provided in a region where the mouthpiece 74 joins the actuator 72 through which air is fed via the aperture 111 into the blister 119 and, via the bypass conduit 118 formed by the spaces between ridges 113, into the mouthpiece 74.

Figure 29:
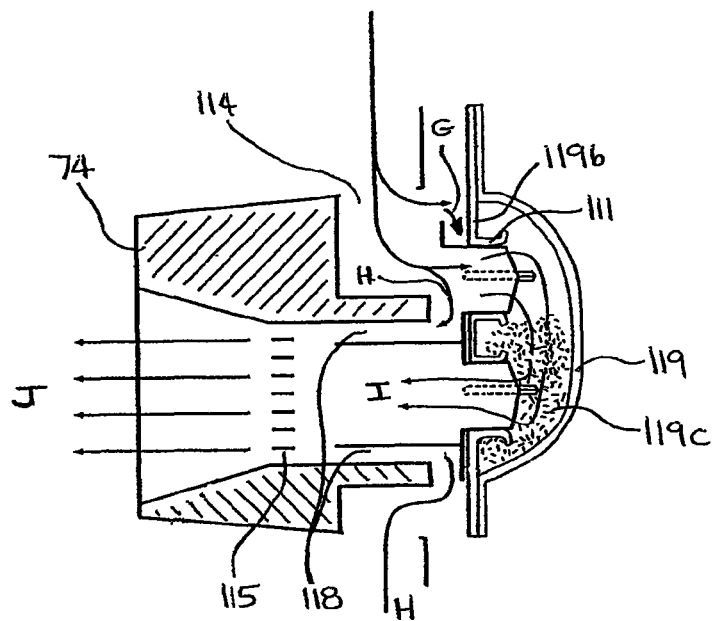
FIG. 29 is a side sectional view to show the passage of air through the piercing head module of FIG. 27.

The airflow through a pierced blister 119 and into the mouthpiece 74 is illustrated schematically in FIG. 29. When a patient inhales through the mouthpiece 74, air is drawn from outside through the holes 114 between the mouthpiece 74 and the actuator 72 from where it flows into the blister 119 through the aperture 111, as indicated by arrow marked "F". In addition to inlet airflow through the aperture 111, air is also drawn into the blister 119 through the space between the lid 119a of the blister 119 and the recessed surface 107a, as indicated by arrow marked "G". In addition to airflow into the blister 119, air is also drawn through the bypass conduit 118 (in the direction of the arrow marked "H") formed by the spaces between the ridges 113 of the tubular section 112 of the piercing head 105 and joins the exit airflow leaving the blister 119 through the aperture 110 in the piercing member 105, in the direction of arrow marked "I". The dose is entrained in the exit airflow and this airflow from the blister 119 together with the air that has flowed into the mouthpiece 74 via the bypass conduit 118 passes through the mesh 115 and out of the device into the patient's airway, in the direction of arrows marked "J".

This embodiment as described has nine moulded components. While this is significantly fewer than other devices with a similar number of doses it is possible to reduce the component count still further. The case halves can, for example, be moulded as a single moulding connected by a moulded-in hinge at the base of the components. In assembly the two halves would be folded together to form the housing. Similarly, the cap and blister door can be integrally moulded.

In addition, as has been described the piercing element can be moulded as part of the actuator. In this way the number of moulded components can be reduced to five or six.

A final embodiment of an inhaler according to the invention will now be described with reference to FIG. 30.

It will be appreciated that it is advantageous for used blisters to be ejected from the device as this results in a smaller and simpler construction. If the device is to retain used blisters, then a take-up spool is required onto which the used blister strip is wound. The obvious disadvantage of a take-up spool is that at all times during use of the device there is an empty space within it. When the device is first used, the take-up spool is empty, and at the end of its life, the feed spool is empty. Accordingly, the device must be made larger to accommodate the blister strip both before and after use.

In an alternative embodiment of the present invention, the inhalation device retains used blisters in a more compact arrangement in which there is no unused space. This is achieved by forming the blister strip into an endless loop and mounting the loop in the housing in a state in which it has been wrapped around itself, as shown in FIG. 30.

Figure 30:
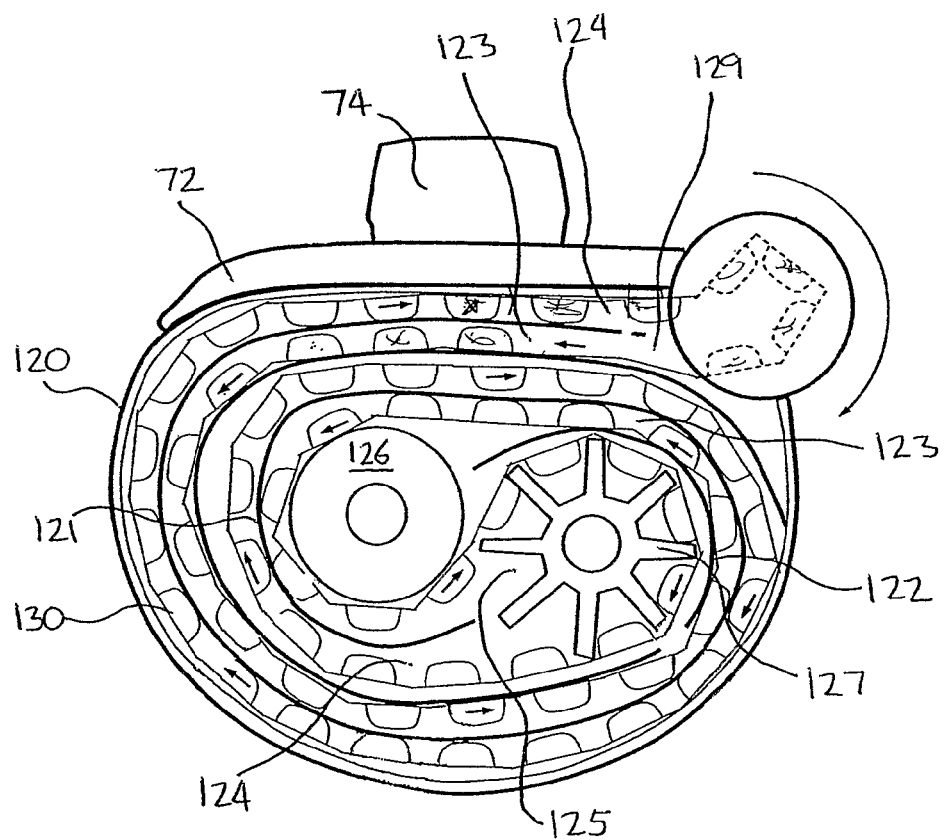
FIG. 30 is a side view of an inhaler having an endless loop drive according to another embodiment of the invention with one half of the housing removed to reveal the internal components.

Referring to FIG. 30, it can be seen that the housing 120 contains two spaced parallel walls 121, 122 to define a pair of parallel spiral channels 123,124 therebetween. The inner end of the channels 123,124 open out into a central chamber region 125 in which is rotatably mounted a feed spool 126 and a feed sprocket 127. The blister strip 130 passes from one channel 123 to the other channel 124 through the chamber region 125 and extends around the feed spool 126 and the feed sprocket 127 in an "S" shaped configuration. The blister strip 130 also passes out of one channel 124 and is wrapped around an indexing wheel (shown generally by reference numeral 128 in FIG. 30) before passing back into the other channel 123. The connections at both ends in effect create a single endless channel for the blister strip 130.

The blister strip 130 may be conventionally formed before its ends are subsequently joined together. If the length of the strip 130 matches the combined length of the two channels 123,124, the strip 130 can be loaded into the channels 123, 124 and located around the teeth (not shown) of the indexing wheel 128 and the inner sprocket 127, as well as being guided around the spool 126.

The indexing wheel 128 indexes the strip 130 via a mouthpiece/actuator arrangement, as has already been described above with reference to FIGS. 20 to 26, although other indexing mechanisms may also be used.

If suitable low friction materials are used, the inner spool 126 and sprocket 127 need not be driven other than by the strip 78 itself. For a long strip 78, or to ensure reliable operation, the spool 126 and sprocket 127 may be connected to the indexing wheel 128 by a simple drive train, belt or similar mechanism (not shown).

As the strip 130 is endless, with regularly spaced blisters, then the user will be able to index the strip 130 indefinitely. Including a blank section 129 in the strip 130 that has no blisters can provide a clear indication that all blisters have been used. This could conveniently be provided at the point where the ends of the strip 130 are joined together. When this blank section 129 of the strip reaches the indexing wheel 128, the strip 78 will no longer be indexed as the indexing wheel 128 rotates, clearly indicating that the strip 130 has been exhausted. In the drawing, the strip 130 is shown with the blank section 129 located just after the indexing wheel 128. This is the position it will be in before the device has been used for the first time.

Many modifications and variations of the invention falling within the terms of the following claims will be apparent to those skilled in the art and the foregoing description should be regarded as a description of the preferred embodiments of the invention only.

The invention claimed is:

1. An inhaler comprising a housing to receive a plurality of blisters each having a puncturable lid and containing a dose of medicament for inhalation by a user, a mouthpiece through which a dose of medicament is inhaled by a user and, an actuator operable to sequentially move each blister into alignment with a blister piercing member, said actuator also being operable to cause the blister piercing member to puncture the lid of an aligned blister such that, when a user inhales through the mouthpiece, an airflow through the blister is generated to entrain the dose contained therein and carry it out of the blister and via the mouthpiece into the user's airway, wherein the housing includes a chamber to receive used blisters, said chamber being covered by a lid attached to the housing which is openable to facilitate removal of a portion of used blisters from the blisters remaining in the inhaler and wherein a slot is formed between the lid and the housing when the lid is closed through which used blisters may protrude when the used blister chamber is full.

2. An inhaler according to claim 1, wherein the actuator is pivotally mounted to the housing.

3. An inhaler according to claim 1, wherein the actuator comprises an arm pivotally mounted to the housing at one end.

4. An inhaler according to claim 3, wherein the blister piercing member depends from one side of said arm positioned so as to extend through an aperture in the housing in a closed position, in which the arm lies substantially against the housing, to pierce the lid of a blister aligned with the blister piercing member.

5. An inhaler according to claim 3, wherein the piercing member comprises at least two discrete piercing heads operable to pierce a corresponding number of holes in a blister aligned with the blister piercing member.

6. An inhaler according to claim 5, wherein an opening is formed in the arm in the vicinity of each piercing head, at least one of said openings forming an airflow inlet into a blister and, at least one other of said openings forming an airflow outlet from a blister.

7. An inhaler according to claim 6, wherein the mouthpiece is on the arm and extends in a direction opposite to the direction in which the piercing heads extend, the openings in the arm being in communication with the inside of the mouthpiece.

8. An inhaler according to claim 6, wherein the mouthpiece includes a primary chamber having an outside air inlet in communication, via the primary chamber, with the or each airflow inlet opening in the arm and, a secondary chamber in communication with the or each airflow outlet opening in said arm such that, when a user inhales through the mouthpiece, air is drawn through the or each airflow inlet opening into the blister via the outside air inlet and the primary chamber to entrain the dose in the airflow, said entrained dose passing through the or each airflow outlet openings into the secondary chamber of the mouthpiece from where it is carried into the user's airway.

9. An inhaler according to claim 8, wherein a partitioning wall separates the primary and secondary chambers within the mouthpiece.

10. An inhaler according to claim 9, wherein at least one air bypass aperture extends through the partitioning wall to communicate the primary chamber with the secondary chamber.

11. An inhaler according to claim 1, comprising an indexing mechanism including an indexing member that moves a blister into alignment with the blister piercing member.

12. An inhaler according to claim 11, wherein the indexing member comprises an indexing wheel that rotates to move a blister into alignment with the blister piercing member.

13. An inhaler according to claim 12, wherein the indexing wheel is configured to rotate to move a blister into alignment with the blister piercing member in response to rotation of the actuator in one direction, movement of the actuator in the opposite direction being operable to puncture the lid of a blister aligned with the blister piercing member.

14. An inhaler according to claim 13, including a cap attached to the housing pivotable between a closed position in which it covers the mouthpiece and an open position in which the mouthpiece is revealed to enable a user to inhale through the mouthpiece.

15. An inhaler according to claim 1 incorporating a coiled strip of blisters, each having a puncturable lid and containing a dose of medicament for inhalation by a user, located in the housing.

16. An inhaler according to claim 15, wherein the strip includes a frangible feature between each blister to facilitate detachment of a blister from an adjacent blister along said line.

17. An inhaler according to claim 15, wherein the strip includes a notch to facilitate tearing of the strip between each blister.

18. A method of using an inhaler according to claim 1, including the step of rotating the actuator to move a blister into alignment with the blister piercing member and to puncture the lid of an aligned blister, inhaling through the mouthpiece to generate an airflow through the blister to entrain the dose contained therein and carry it via the mouthpiece into the user's airway, the method also including the step of opening the lid covering the chamber to remove a portion of the used blisters from the blisters remaining in the device.

19. A method according to claim 18, wherein the step of rotating the actuator includes the step of rotating it in a first direction to move a blister into alignment with the blister piercing member and, rotating it in a second direction to puncture the lid of the blister aligned with the blister piercing member.

* * * * *